United States Patent
Earle et al.

(10) Patent No.: US 8,664,460 B2
(45) Date of Patent: Mar. 4, 2014

(54) OLIGOMERISATION WITH INDIUM (III) CHLORIDE

(75) Inventors: Martyn John Earle, Belfast (GB); Johanna Kärkkäinen, Belfast (GB); Natalia V. Plechkova, Belfast (GB); Alina Tomaszowska, Belfast (GB); Kenneth Richard Seddon, Belfast (GB)

(73) Assignee: The Queen's University of Belfast, Belfast, North Ireland (GB)

( * ) Notice: Subject to any disclaimer, the term of this patent is extended or adjusted under 35 U.S.C. 154(b) by 709 days.

(21) Appl. No.: 12/096,683

(22) PCT Filed: Dec. 12, 2006

(86) PCT No.: PCT/GB2006/004639
§ 371 (c)(1), (2), (4) Date: Aug. 19, 2008

(87) PCT Pub. No.: WO2007/068910
PCT Pub. Date: Jun. 21, 2007

(65) Prior Publication Data
US 2008/0306319 A1 Dec. 11, 2008

(30) Foreign Application Priority Data
Dec. 12, 2005 (GB) .................. 0525251.5

(51) Int. Cl.
C07C 2/22 (2006.01)
(52) U.S. Cl.
USPC .......... 585/521; 585/502; 585/510; 585/511; 585/514; 585/520; 585/527

(58) Field of Classification Search
USPC .......... 585/510, 511, 520, 521, 527, 502, 514
See application file for complete search history.

(56) References Cited

U.S. PATENT DOCUMENTS

| | | | | |
|---|---|---|---|---|
| 5,463,158 A | * | 10/1995 | Goledzinowski et al. .... | 585/520 |
| 5,550,306 A | * | 8/1996 | Chauvin et al. ............... | 585/514 |
| 5,693,585 A | | 12/1997 | Benazzi et al. | |
| 5,731,101 A | * | 3/1998 | Sherif et al. .................. | 429/102 |
| 6,673,737 B2 | * | 1/2004 | Mehnert et al. ............... | 502/159 |

(Continued)

FOREIGN PATENT DOCUMENTS

| EP | 0553009 A1 | 1/1993 |
|---|---|---|
| EP | 1120159 A1 | 1/2001 |

(Continued)

OTHER PUBLICATIONS

Valkenberg, et al., "Immobilisation of Ionic Liquids on Solid Supports" in Green Chemistry, 2002, 4, 88-93—available on-line Dec. 2001.*

(Continued)

Primary Examiner — In Suk Bullock
Assistant Examiner — Bradley Etherton
(74) Attorney, Agent, or Firm — David W. Carstens; Carstens & Cahoon, LLP

(57) ABSTRACT

The application discloses novel processes for the oligomerization of unsaturated hydrocarbons, and more specifically the use of selected ionic liquids containing Indium (III) Chloride in the oligomerization of unsaturated hydrocarbons, which allows for selection of the oligomers formed.

39 Claims, 12 Drawing Sheets

(56) References Cited

U.S. PATENT DOCUMENTS

| | | | |
|---|---|---|---|
| 6,969,693 B2 * | 11/2005 | Sauvage et al. | 502/159 |
| 2005/0054694 A1 * | 3/2005 | Seddon et al. | 514/362 |
| 2005/0113621 A1 * | 5/2005 | Hope et al. | 585/521 |

FOREIGN PATENT DOCUMENTS

| | | | | |
|---|---|---|---|---|
| FR | 2861084 A1 | 10/2003 | | |
| GB | 2398573 A | 8/2004 | | |
| WO | WO 9521872 A1 * | 8/1995 | | C08F 4/52 |
| WO | WO-9850153 A1 * | 11/1998 | | B01J 31/02 |
| WO | 99/03163 A1 | 1/1999 | | |
| WO | WO 9903163 A1 * | 1/1999 | | H01M 6/30 |
| WO | 01/32308 A1 | 5/2001 | | |
| WO | 02/098560 A1 | 12/2002 | | |
| WO | 03/028883 A1 | 4/2003 | | |
| WO | 03/089390 A2 | 10/2003 | | |

OTHER PUBLICATIONS

Gordon, et al., "Lewis Acids" in The Chemist's Companion, John Wiley & Sons, 1972, pp. 54-56—month unknown.*

Kim, et al., "Tetrahaloindate (III)-Based Ionic Liquids in the Coupling Reaction of Carbon Dioxide and Epoxides to Generate Cycic Carbonates: H-Bonding and Mechanistic Studies," Sep. 7, 2005, pp. 7882-7891, vol. 70, Journal of Organic Chemistry, American Chemical Society, Easton, US.

da Silveira Neto, et al., "Organoindate Room Temperature Ionic Liquid: Synthesis, Physicochemical Properties and Application," May 10, 2004, pp. 1155-1158, No. 8, Synthesis, Georg Thieme Verlag Stuttgart, New York, US.

Chauvin, et al., "Oligomerization of n-Butenes Catalyzed by Nickel Complexes Dissolved in Organochloroaluminate Ionic Liquids," Jan. 15, 1997, pp. 275-278, vol. 165, Journal of Catalysis, Academic Press, Minnesota, US.

* cited by examiner

OLIGOMERISATION WITH INDIUM (III) CHLORIDE

The present invention relates to the oligomerisation of unsaturated hydrocarbons, and more specifically to the use of specifically selected ionic liquids in the oligomerisation of unsaturated hydrocarbons.

The synthesis of polymers by polymerization of alkene monomers is a well known, and exceedingly important, reaction in the chemical industry.

However, many of the reactions require the use of toxic solvents, for example, hydrogen fluoride, which are highly hazardous to the environment. Other reactions make use of catalysts which may suffer poisoning and deactivation, thereby quickly rendering them of little use.

Given the volume of polymers and oligomers produced each year, there is a need to develop cleaner, safer and more efficient processes for carrying out polymerisation or oligomerisation on an industrial scale.

Ionic liquids are a novel class of solvents which have been developed over the last few years. The term "ionic liquid" as used herein refers to a liquid that is capable of being produced by melting a solid, and when so produced consists solely of ions. Ionic liquids may be derived from organic salts.

An ionic liquid may be formed from a homogeneous substance comprising one species of cation and one species of anion, or it can be composed of more than one species of cation and/or anion. Thus, an ionic liquid may be composed of more than one species of cation and one species of anion. An ionic liquid may further be composed of one species of cation, and one or more species of anion. Thus, the mixed salts used in the present invention can comprise mixed salts containing anions and cations.

The main advantages of ionic liquids compared to molecular solvents are their non-volatility, low toxicity, low flammability, applicability at wide temperature ranges and the possibility of recycling, which properties make them environmentally friendly. Such solvents are of course greatly desired for industrial processes. In addition, because of their ionic structure, they often change the reactivity of common reagents or the regio- or stereoselectivity of reactions resulting in faster reactions and higher yields.

The term "ionic liquid" includes compounds having both high melting temperature and compounds having low melting points, e.g. at or below room temperature (i.e. 15 to 30° C.). The latter are often referred to as "room temperature ionic liquids" and often derived from organic salts having pyridinium and imidazolium-based cations. As mentioned above, a feature of ionic liquids is that they have particularly low (essentially zero) vapour pressures. Many organic ionic liquids have low melting points, for example, less than 100° C., particularly less than 100° C., and around room temperature, e.g. 15 to 30° C., and some have melting points well below 0° C. For the purposes of the present invention, it is desirable that the organic ionic liquid has a melting-point of 250° C. or less, preferably 150° C. or less, more preferably 100° C. and even more preferably 80° C. or less, although any compound that meets the criteria of being a salt consisting of an anion and cation, which is liquefied at or near the reaction temperature, or exists in a fluid state during any stage of the reaction can be defined as an organic ionic liquid especially suitable for use in the processes of the present invention.

According to the present invention, there is provided a selective process for the oligomerisation of unsaturated hydrocarbons, characterised in that the reaction takes place in the presence of an indium (III) chloride ionic liquid or other acidic or Lewis acidic ionic liquid.

The reactions of the present invention are particularly suitable for producing dimers, trimers and/or tetramers.

Further, the reactions of the present invention may be used to selectively produce dimers, trimers and/or tetramers, and are particularly useful in the production of trimers and tetramers, and even more preferably trimers.

In accordance with the present invention there is provided a selective oligomerisation process, wherein the indium(III) chloride ionic liquid may be represented by the formula:

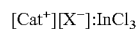

wherein $X^-$ is an anionic species; and $Cat^+$ is a cationic species selected from:
a heterocyclic ring structure selected from imidazolium, pyridinium, pyrazolium, thiazolium, isothiazolinium, oxothiazolium, oxazinium, oxazolium, dithiazolium, triazolium, selenozolium, oxaphospholium, furanium, thiophenium, phospholium, pentazolium, indolium, indolinium, iso-oxazolium, iso-triazolium tetrazolium, benzofuranium, thiadiazolium, pyrimidinium, pyrazinium, pyridazinium, piperazinium, piperidinium, morpholinium, pyranium, phthalazinium, quinazolinium, quinolinium, isoquinolinium, pyrrolidinium, diazabicycloundecenium, diazabicyclononenium, diazabicyclodecenium, and triazadecenium; or

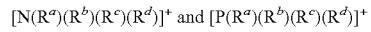

wherein: $R^a$, $R^b$, $R^c$, and $R^d$ can be the same or different, and are each independently selected from a $C_1$ to $C_{40}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_6$ to $C_{10}$ aryl, CN, OH, $NO_2$, $C_7$ to $C_{30}$ aralkyl and $C_7$ to $C_{30}$ alkaryl. $Cat^+$ may be selected from: —

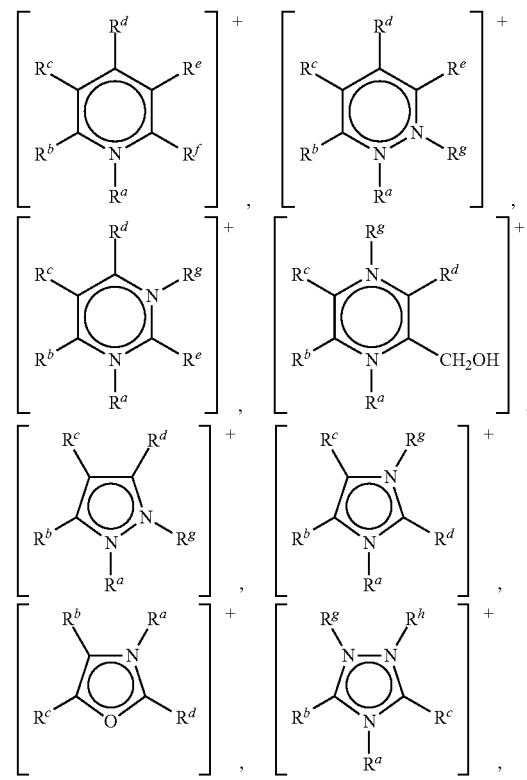

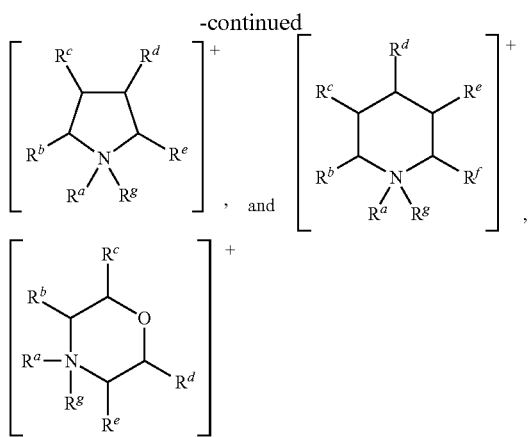

wherein: $R^a$, $R^b$, $R^c$, $R^d$, $R^e$, $R^f$, $R^g$ and $R^h$ can be the same or different, and are each independently selected from hydrogen, a $C_1$ to $C_{40}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_6$ to $C_{10}$ aryl, CN, OH, $NO_2$, $C_7$ to $C_{30}$ aralkyl and $C_7$ to $C_{30}$ alkaryl, or any two of $R^b$, $R^c$, $R^d$, $R^e$ and $R^f$ attached to adjacent carbon atoms form a methylene chain —$(CH_2)_q$— wherein q is from 8 to 20.

Preferably, $Cat^+$ is selected from:

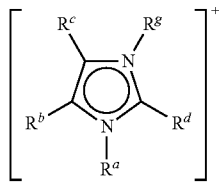

wherein: $R^a$, $R^b$, $R^c$, $R^d$, and $R^g$ are as defined above.

More preferably, $R^b$, $R^c$ and $R^d$ are each hydrogen; and $R^a$ and $R^g$ are selected from $C_1$ to $C_{20}$, linear or branched, alkyl, and one of $R^a$ and $R^g$ may be hydrogen.

Still more preferably, one of $R^a$ and $R^g$ is hydrogen or methyl; and the other is selected from $C_1$ to $C_{20}$ linear or branched alkyl.

Even more preferably, one of $R^a$ and $R^g$ is hydrogen or methyl, and the other is selected from $C_1$ to $C_{18}$ linear or branched alkyl.

Yet more preferably, one of $R^a$ and $R^g$ is hydrogen or methyl, and the other is selected from methyl, ethyl, butyl, hexyl, octyl, decyl, dodecyl, tetradecyl, hexadecyl and octadecyl.

Most preferably, the ionic liquid is selected from: methylimidazolium chloroindate (III), 1,3-dimethylimidazolium chloroindate (III), 1-ethyl-3-dimethylimidazolium chloroindate (III), 1-butyl-3-dimethylimidazolium chloroindate (III), 1-hexyl-3-methylimidazolium chloroindate (III), 1-octyl-3-methylimidazolium chloroindate (III), 1-decyl-3-methylimidazolium chloroindate (III), 1-dodecyl-3-methylimidazolium chloroindate (III), 1-methyl-3-tetradecylimidazolium chloroindate (III), 1-hexadecyl-3-methylimidazolium chloroindate (III) and 1-methyl-3-octadecylimidazolium chloroindate (III) tetraalkylammonium, chloroindate(III), tetraalkylphosphonium, chloroindate(III).

$Cat^+$ may also preferably be selected from:

$[N(R^a)(R^b)(R^c)(R^d)]^+$ and $[P(R^a)(R^b)(R^c)(R^d)]^+$ wherein: $R^a$, $R^b$, $R^c$, and $R^d$ can be the same or different, and are each independently selected from, a $C_1$ to $C_{20}$, straight chain or branched alkyl group, a $C_3$ to $C_6$ cycloalkyl group, or a $C_6$ to $C_8$ aryl group, wherein said alkyl, cycloalkyl or aryl groups are unsubstituted or may be substituted by one to three groups selected from: $C_1$ to $C_6$ alkoxy, $C_6$ to $C_{10}$ aryl, CN, OH, $NO_2$, $C_7$ to $C_{30}$ aralkyl and $C_7$ to $C_{30}$ alkaryl. $R^a$, $R^b$, $R^c$, and $R^d$ may also be selected from hydroxyethyl, $R^a$, $R^b$, $R^c$, and $R^d$ may also be selected from hydroxyethyl, hydroxymethyl, hydroxypropyl, hydroxybutyl, polyethyleneglycol ethers such as (—$CH_2$—$CH_2$—O—)$_n$(OCH$_3$), (—$CH_2$—$CH_2$—O—)$_n$(OC$_2$H$_5$), (—$CH_2$—$CH_2$—O—)$_n$(OC$_m$H$_{2m+1}$), where n=1, 2, 3, 4, 5, 6, 7, 8, 9, 10 and m=0, 1, 2, 3, 4, 5, 6, 7, 8, 9, 10, 11, 12, 13, 14, 15, 16, 17, 18.

Even more preferably, $Cat^+$ is selected from: triethylhexylammonium, tetrabutylammonium, trihexyltetradecyl phosphonium, cholinium [(CH$_3$)$_3$N—CH$_2$CH$_2$OH], methylcholinium [(CH$_3$)$_3$N—CH$_2$CH$_2$OCH$_3$], ethylcholinium [(CH$_3$)$_3$N—CH$_2$CH$_2$OC$_2$H$_5$], propylcholinium [(CH$_3$)$_3$N—CH$_2$CH$_2$OC$_3$H$_7$].

In a preferred embodiment of this invention, the ionic liquid is Lewis-acidic, acidic or neutral.

Where $Cat^+$ is selected from:

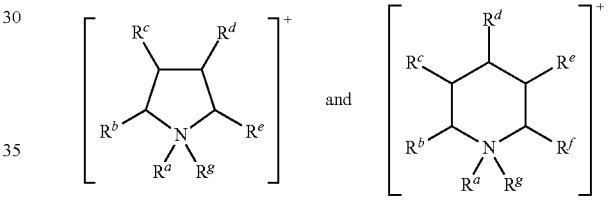

$R^a$, $R^b$, $R^c$, $R^d$, $R^e$, $R^f$, and $R^g$ are preferably as defined above, with the proviso that $R^a$ and $R^g$ are not hydrogen.

Where $Cat^+$ is:

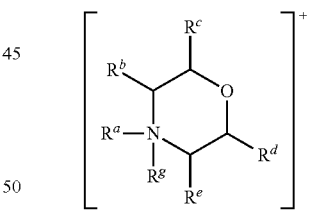

$R^a$, $R^b$, $R^c$, $R^d$, $R^e$, and $R^g$ are preferably as defined above, with the proviso that $R^a$ and $R^g$ are not hydrogen.

Preferably the ionic liquids of the present invention are composed of a single species of cation.

The cationic species $Cat^+$ may be neutral, acidic or basic.

For the ionic liquids of the present invention, the anion $X^-$ may by selected from: halide, i.e. $F^-$, $Cl^-$, $Br^-$, $I^-$, $HSO_4^-$, $H_2PO_4^-$, $HPO_4^{2-}$, $OSO_2CH_3^-$, $OSO_2(C_6H_4)CH_3^-$, $OSO_3CH_3^-$, $OSO_3C_2H_5^-$ or $SO_4^{2-}$.

Preferably, $X^-$ is $Cl^-$ or $Br^-$, and most preferably $Cl^-$.

Preferably, the ionic liquids of the present invention are composed of a single species of anion.

Also preferably, the ionic liquids of the present invention are composed of a single species of cation and a single species of anion.

In accordance with the processes of the present invention, the unsaturated hydrocarbon may be an optionally substituted, $C_2$ to $C_{20}$ linear or branched alkene.

Preferably, the unsaturated hydrocarbon is a $C_2$ to $C_{10}$ linear or branched alkene.

More preferably, the unsaturated hydrocarbon is a $C_2$ to $C_5$ linear or branched alkene. Still more preferably, the unsaturated hydrocarbon is isobutene.

The polymerization processes of the present invention relate to polymerization in general, and to more controlled aspects of polymerization, for example, dimerisation, trimerisation, quaternisation etc. Preferably, the processes of the present invention are used for dimerisation, trimerisation and quaternisation to produce dimers, trimers and tetramers. More preferably, the processes of the present application are used to produce trimers and tetramers, and most preferably trimers.

In accordance with one aspect of the present invention, the ionic liquid acts as both a catalyst and a solvent.

The term "catalyst" is used herein to include all forms of catalysis, including classic initiators, co-initiators, co-catalysts, activating techniques etc.

A particular advantage of the processes of the present invention is that the ionic liquid may be easily separated from the reaction products as a separate layer or separate phase. Further, the catalyst (for example chloroindate (III) ionic liquid) may be reused repeatedly, without the need for complicated purification steps or regeneration, although if necessary, further purification steps may be carried out in order to optimize the catalyst purity/efficiency.

In accordance with another aspect of the present invention, the ionic liquids may be retained on a solid support, and act as a catalyst.

Suitable support materials especially include particulated metal oxides, oxides of silicon or germanium, polymers, and mixtures thereof. Examples include alumina, silica, aluminosilicates, clay, $TiO_2$, zeolites and particulated polyolefins. Preferably, the solid support is silica.

A further aspect of the present invention includes a process for producing a supported ionic liquid, comprising the steps of:
dissolving the ionic liquid in a solvent;
adding a solid support; and
removing the solvent.

Any suitable organic solvent may be used, and preferably the solvent is methanol.

The solid support may include particulated metal oxides, oxides of silicon or germanium, polymers, and mixtures thereof. Examples include alumina, silica, aluminosilicates, clay, and particulated polyolefins. Preferably, the solid support is silica.

The solvent may be removed using suitable known means, but is preferably removed by evaporation.

Preferably, the supported ionic liquid is heated under reduced pressure. More preferably, the supported ionic liquid is heated to 100° C. for 1 hour at a pressure of 133.3 Pa (1 mmHg).

The present application also discloses supported ionic liquids, and their inventive use as catalysts in selective chemical reactions, preferably selective oligomerisation processes.

The supported ionic liquids of the present invention are particularly useful as: they remain catalytically active; no leaching of indium or other metal ions are observed; they are water and moisture tolerant; easy to use and prepare; allow control of product distribution.

Methods for oligomerising unsaturated hydrocarbons are disclosed in the examples of the present application. It will be appreciated that other known suitable methods exist, all of which are within the knowledge of the person skilled in the art.

In undertaking an oligomerisation reaction in accordance with the present invention, the ionic liquid preferably comprises greater than 0.5 mol fraction $InCl_3$ more preferably greater than or equal to 0.52 mol fraction. The mol fraction of $InCl_3$ is represented herein by $x(InCl_3)$.

The ionic liquid may also comprise greater than or equal to 0.55 mol fraction $InCl_3$, 0.57 mol fraction, 0.58 mol fraction, or 0.60 mol fraction or 0.67 mol fraction depending on the rate of reaction required.

In general, the greater the amount of $InCl_3$ present, the faster the rate at which the oligomerisation reaction occurs.

Also, the greater the amount of $InCl_3$ present (i.e. the stronger the catalyst), the greater the amount of longer oligomers which are formed, for example, pentamers, hexamers, heptamers etc.

The processes of the present invention are generally temperature sensitive, with an increase in temperature causing an increase in reaction rate.

For reactions carried out with unsupported ionic liquids:—
Where $InCl_3$ is present in the ionic liquid in an amount of greater than 0.5 mol fraction, the reaction temperature is preferably 120° C., or above. In general, the greater the amount of, for example, $InCl_3$ which is present, the lower the necessary reaction temperature.

Where the concentration of $InCl_3$ is 0.55 mol fraction, the temperature needed for the reaction to occur is approximately 80° C. For concentrations of 0.58 mol fraction or greater, the temperature needed for the reaction to occur is approximately 20° C., i.e. about room temperature.

When the process is used for producing dimers, the mole fraction of $InCl_3$ in the ionic liquid is preferably greater than 0.50, more preferably from 0.50-0.55. The reaction-temperature is preferably at least 80° C., and more preferably at least 120° C.

For producing trimers and/or tetramers, the mole fraction of $InCl_3$ in the ionic liquid is preferably greater than 0.50, and more preferably from 0.50-0.67. The reaction temperature is preferably at least 20° C.

Where the ionic liquid is supported, for example, on silica, the ionic liquid may be present in an amount of greater than 5 wt %, preferable greater than 15 wt %, more preferably greater than or equal to 20 wt %. The ionic liquid may also be present in amounts up to 40 wt % and higher.

BRIEF DESCRIPTION OF THE DRAWINGS

The present invention will now be discussed by way of example and with reference to the following figures.

1. EXPERIMENTAL DETAILS

Figure 1:
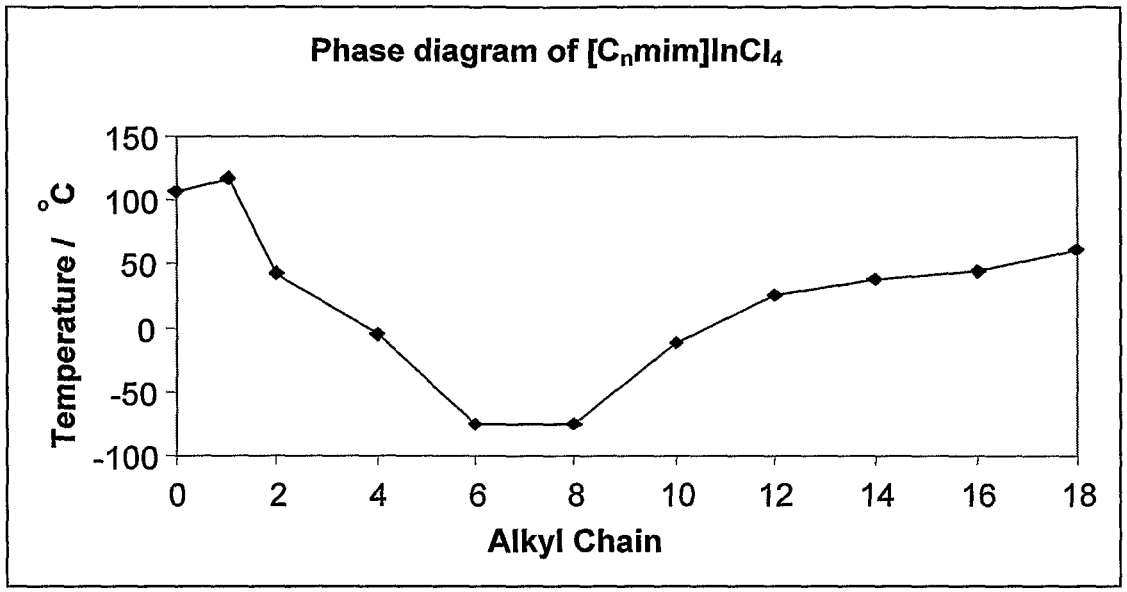
FIG. 1 shows a phase diagram for the salts of the present invention as a function of chain length.

[C$_n$-mim]Cl's were prepared by a quaternarisation reaction from 1-methylimidazole and the appropriate haloalkane by procedures described in the literature (and known to the skilled person), and the ionic liquids formed were dried under high vacuum before use.

[C$_2$mim]Cl was prepared and dried before use under high vacuum.

Indium(III)chloride (99% and 98%) and isobutene (99%) were purchased from Aldrich and used as received.

$^1$H and $^{13}$C spectra were recorded on Bruker DPX300 spectrometer in CD$_3$CN or in CDCl$_3$. Proton and carbon chemical shifts are recorded relative to an internal TMS standard.

Elemental analyses were performed by A.S.E.P. at the Queens University of Belfast.

Viscosities were measured by a Brookfield DV-II+ viscometer.

The melting points, cold crystallisation and glass transitions temperatures were determined by differential scanning calorimetry, Perkin-Elmer Pyris 1 DSC equipped with dinitrogen cryostatic cooling or Perkin-Elmer Pyris 7, samples were 10-20 mg and heating and cooling rates 10° C. min$^{-1}$. Samples were placed in an aluminium pan and an empty aluminium pan was used as the reference.

Microscopic analysis of [C$_2$mim]Cl+InCl$_3$ was done using a Wishart Scientific Olympus BX50 polarizing microscope and photos were taken with a JVC colour video camera TK-1085E.

Products from dimerization reactions were analysed with Perkin-Elmer Turbomass GCMS (column RTX5, 60 m, 0.25 mm).

2. PREPARATION OF ALKYLMETHYLIMIDAZOLIUM CHLOROINDATE(III) IONIC LIQUIDS

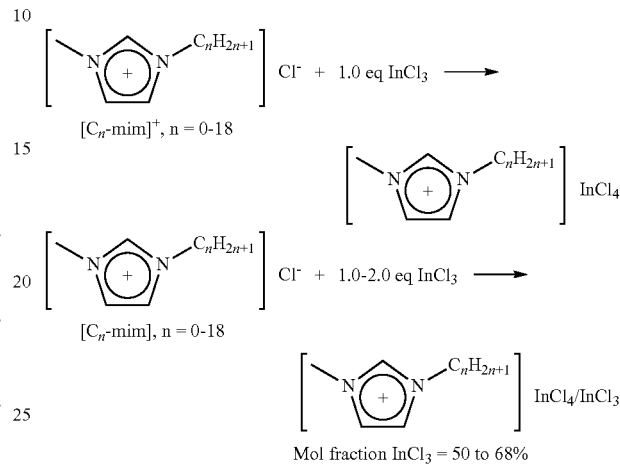

2.1. General Synthesis 1-alkyl-3-methylimidazolium chloroindate (III) salts with the general formula [C$_n$-mim][InCl$_4$] (n=0, 1, 2, 4, 6, 8, 10, 12, 14, 16 and 18) were prepared from [C$_n$-mim]Cl and indium(III) chloride, InCl$_3$. Both starting materials are quite hygroscopic and for that reason reactions were carried under a nitrogen atmosphere. Before use [C$_n$-mim]Cl was dried under high vacuum for a night. InCl$_3$ was used without purification. The equivalent amounts of solid starting materials were mixed in a round bottom flask. The reaction is not very exothermic and in order to get a homogenous reaction mixture it has to be heated with an oil bath. In comparison, the preparation of chloroaluminates is a very exothermic reaction and aluminium(III) chloride has to be added in a small batches into [C$_n$-mim]Cl otherwise the product might decompose. The formed [C$_n$-mim]AlCl$_4$ is also air and water sensitive and the reaction has to be done in a glove box. The chloro(III)indates, which have been synthesized are air and water stable. The temperature of the oil bath was adjusted with the melting point of [C$_n$-mim]Cl and the reaction mixture was stirred for a while after the homogenous mixture was formed. After reacting, the product was allowed to cool down to room temperature. Finally all products were dried under high vacuum. [Hmim][InCl$_4$] and [C$_1$mim][InCl$_4$] crystallized on cooling. C$_4$, C$_6$, C$_8$ and C$_{10}$ are liquids at room temperature. C$_{16}$ and C$_{18}$ crystallized when the product was dried under high vacuum. [C$_2$mim][InCl$_4$], C$_{12}$ and C$_{14}$ crystallized on standing in a freezer.

2.2 Analysis

2.2.1 $^1$H-NMR, $^{13}$C-NMR and Elemental Analyses

1-Alkyl-3-methylimidazolium chloroindate(III) salts were obtained as white solids (n=0, 1 and 12-18) or colourless to pale yellow liquids (n=4-10). Salts were characterized by a combination of $^1$H-NMR, $^{13}$C-NMR and elemental analysis.

The $^1$H and $^{13}$C data is summarized in Tables 1 and 2, respectively. $^1$H and $^{13}$C NMR spectra are very similar for all chloroindate(III) salts. Also the chemical shift of the C(2)-H protons are all remarkably similar and do not show the large downfield shift related to hydrogen bonding observed for the chloride salts. CDCl$_3$ was used as a solvent, but [Hmim][InCl$_4$] and [C$_1$mim][InCl$_4$] didn't dissolve into it so their NMR's were measured in CD$_3$CN solutions.

TABLE 1

$^1$H NMR spectra of chloroindate(III) salts.

| N | H2 | H4 | H5 | NCH2 | NCH3 | NCH2CH2 | Alkyl | Terminal CH3 |
|---|----|----|----|------|------|---------|-------|--------------|
| 0 | 8.44 (s) | 7.35 (s) | 7.35 (s) | | 3.85 (s) | 2.93 (s) C—H | | |
| 1 | 8.34 (s) | 7.32 (s) | 7.31 (s) | | 3.82 (s) | | | |
| 2 | 8.69 (s) | 7.31 (d, J = 1.8) | 7.30 (d, J = 1.8) | 4.32 (q, J = 7.5) | 4.03 (s) | | | 1.63 |
| 4 | 8.58 (s) | 7.33 (d, J = 1.8) | 7.31 (d, J = 1.8) | 4.23 (t, J = 7.5) | 4.01 (s) | 1.91 (m, J = 7.5) | 1.42 (2 H m, J = 7.5) | 1.00 (t, J = 7.4) |
| 6 | 8.62 (s) | 7.35 (d, J = 1.8) | 7.33 (d, J = 1.8) | 4.22 (t, J = 7.5) | 4.01 (s) | 1.91 (m, J = 7.5) | 1.33 (6 H m) | 0.89 (t, J = 7.0) |
| 8 | 8.57 (s) | 7.37 (d, J = 1.8) | 7.35 (d, J = 1.8) | 4.22 (t, J = 7.5) | 4.00 (s) | 1.91 (m, J = 7.5) | 1.33 (10 H m) | 0.87 (t, J = 7.0) |
| 10 | 8.51 (s) | 7.37 (d, J = 1.8) | 7.35 (d, J = 1.8) | 4.21 (t, J = 7.5) | 4.00 (s) | 1.91 (m, J = 7.2) | 1.33 (14 H m) | 0.88 (t, J = 7.0) |
| 12 | 8.58 (s) | 7.36 (d, J = 1.8) | 7.34 (d, J = 1.8) | 4.21 (t, J = 7.5) | 4.00 (s) | 1.91 (m, J = 7.2) | 1.33 (18 H m) | 0.88 (t, J = 7.0) |
| 14 | 8.54 (s) | 7.35 (d, J = 1.8) | 7.33 (d, J = 1.8) | 4.20 (t, J = 7.5) | 4.00 (s) | 1.91 (m, J = 7.2) | 1.34 (22 H m) | 0.88 (t, J = 7.0) |
| 16 | 8.62 (s) | 7.36 (d, J = 1.8) | 7.32 (d, J = 1.8) | 4.22 (t, J = 7.5) | 4.00 (s) | 1.91 (m, J = 7.2) | 1.33 (26 H m) | 0.88 (t, J = 7.0) |
| 18 | 8.53 (s) | 7.35 (d, J = 1.8) | 7.33 (d, J = 1.8) | 4.21 (t, J = 7.5) | 4.00 (s) | 1.91 (m, J = 7.2) | 1.33 (30 H m) | 0.88 (t, J = 7.0) |

TABLE 2

$^{13}$C NMR spectra of chloroindate(III) salts.

| N | 0 | 1 | 2 | 4 | 6 | 8 | 10 | 12 | 14 | 16 | 18 |
|---|---|---|---|---|---|---|----|----|----|----|----|
| CH3 | | | 15.61 | 13.17 | 13.97 | 14.06 | 14.11 | 14.18 | 14.23 | 14.22 | 14.22 |
| CH2 | | | | 19.14 | 22.32 | 22.50 | 22.61 | 22.72 | 22.78 | 22.77 | 22.78 |
| | | | | 31.54 | 25.84 | 26.15 | 26.19 | 26.31 | 26.37 | 26.36 | 26.36 |
| | | | | | 29.98 | 28.77 | 28.85 | 28.97 | 29.02 | 29.03 | 29.02 |
| | | | | | 30.95 | 28.88 | 29.18 | 29.39 2C | 29.44 3C | 29.45 2C | 29.45 2C |
| | | | | | | 29.99 | 29.27 | 29.55 | 29.60 | 29.62 | 29.62 |
| | | | | | | 31.57 | 29.39 | 29.64 2C | 29.70 3C | 29.79 6C | 29.80 8C |
| | | | | | | | 30.01 | 30.12 | 30.172 | 30.18 | 30.15 |
| | | | | | | | 31.79 | 31.95 | 32.00 | 32.00 | 32.01 |
| NCH3 | 36.75 | 36.86 2C | 37.19 | 36.76 | 37.09 | 37.03 | 37.07 | 37.16 | 37.23 | 37.21 | 37.23 |
| NCH2 | | | 45.75 | 49.99 | 50.60 | 50.55 | 50.61 | 50.70 | 50.78 | 50.72 | 50.78 |
| CH | 120.52 | | 122.49 | 122.45 | 122.64 | 122.58 | 122.64 | 122.65 | 122.68 | 122.62 | 122.71 |
| CH | 124.17 | 124.48 2C | 124.13 | 123.71 | 124.02 | 123.96 | 124.02 | 124.07 | 124.11 | 124.08 | 124.14 |
| CH | 136.15 | 137.28 | 134.85 | 134.36 | 134.97 | 134.86 | 134.76 | 135.04 | 135.12 | 135.20 | 135.00 |

Data from elemental analyses is summarised in Table 3. Results are very good for salts with $C_n>1$, but [Hmim][InCl$_4$] contains some amount of water. Calculated elemental values for [Hmim][InCl$_4$] are (%): C, 14.14; H, 2.08; N, 8.25; Cl, 41.74; In, 33.80. And for [Hmim][InCl$_4$]×1 H$_2$O salt: C, 13.43; H, 2.54; N, 7.83; Cl, 39.64; In, 32.09; O, 4.47. Results that were found from elemental analysis were between these calculated values. Found: C, 13.42; H, 2.60; N, 7.32; Cl, 41.44; In, 33.41. Water contents of these salts could not been measured with Karl-Fisher titration measurements because of the nature of anion.

TABLE 3

Elemental analysis data C, H, N, Cl and In for chloroindate(III) salts. Found elemental value (%) is given first and calculated value in parentheses.

| N | C | H | N | Cl | In |
|---|---|---|---|---|---|
| 0 | 13.42 (14.14) | 2.60 (2.08) | 7.32 (8.25) | 41.44 (41.74) | 33.41 (33.80) |
| 1 | 17.18 (16.96) | 2.71 (2.56) | 7.95 (7.92) | 32.35 (32.46) | 40.18 (40.09) |
| 2 | 20.04 (19.59) | 3.35 (3.01) | 7.80 (7.62) | 38.46 (38.56) | 30.70 (31.22) |
| 4 | 24.20 (24.27) | 3.82 (3.82) | 7.18 (7.08) | 35.87 (35.82) | 29.50 (29.01) |
| 6 | 28.72 (28.33) | 4.57 (4.52) | 6.93 (6.61) | 32.69 (33.45) | 28.34 (27.09) |
| 8 | 32.15 (31.89) | 5.08 (5.13) | 6.71 (6.20) | 31.98 (31.38) | 26.85 (25.40) |
| 10 | 35.08 (35.03) | 5.36 (5.67) | 5.80 (5.84) | 29.76 (29.54) | 24.18 (23.92) |
| 12 | 38.03 (37.82) | 5.76 (6.15) | 5.56 (5.51) | 28.08 (27.91) | 22.72 (22.60) |
| 14 | 40.79 (40.33) | 6.49 (6.58) | 5.23 (5.23) | 26.08 (26.45) | 21.18 (21.42) |
| 16 | 42.50 (42.58) | 6.62 (6.97) | 5.07 (4.97) | 24.81 (25.14) | 20.04 (20.35) |
| 18 | 44.46 (44.62) | 6.91 (7.32) | 4.53 (4.73) | 23.16 (23.95) | 20.03 (19.39) |

2.2.2 Thermal Analysis

The thermal behaviour of the chloroindate(III) salts was characterized by differential scanning calorimetry (DSC). The melting, glass transitions and cold crystallisation points of the salts are shown in Table 4 below. Glass transitions and melting points were determined from the peak positions for the heating cycle. The end values of the transition peaks are given in parentheses and transition enthalpies are also reported. The cold crystallisation points were determined from the peak positions for the cooling cycle and the transition enthalpies are also reported. Results are reproducible. Some variations of transition points were seen only with samples [C$_{12}$mim][InCl$_4$] and [C$_{14}$mim][InCl$_4$], [Hmim][InCl$_4$], [C$_1$mim][InCl$_4$], [C$_2$mim][InCl$_4$] and salts with n>12 have true melting points and they crystallised on cooling or standing in a freezer. The following ionic liquids; [C$_4$mim][InCl$_4$], [C$_6$mim][InCl$_4$], [C$_8$mim][InCl$_4$] and [C$_{10}$mim][InCl$_4$] show a strong tendency to supercool, forming more viscous liquids, and finally glasses. The DSC analysis of these $C_n$: 4-10 ionic liquids didn't show cold crystallizations. The glass transition temperatures of these ionic liquids are between −75° C. and −80° C. The true melting point of IL's start to rise again when alkyl chain length was above 10. The phase diagram for the salts as a function of chain length is illustrated in FIG. 1. The phase diagram shows the same trend that has been seen before with other imidazolium based ionic liquids, for example [C$_n$-mim][BF$_4$]. Enthalpies of melting and cold crystallisations varied from 10 to 110, but enthalpy of melting and enthalpy of cold crystallisation in certain samples were quite comparable. Enthalpies of glass transitions were small ca. 1 J/g.

Thermal data from DSC for chloroindate(III) salts. Transition temperatures (° C.) are measured from peak positions for glass transitions (T$_{gt}$), melting points (T$_{mp}$) and cold crystallization (T$_{cc}$). End values are given in paretheses for T$_{cc}$ and T$_{mp}$ also transition enthalpy, ΔH, is shown (J/g)

TABLE 4

Thermal data from DSC for chloroindate(III) salts. Transition temperatures (° C.) are measured from peak positions for glass transitions (T$_{gt}$), melting points (T$_{mp}$) and cold crystallization (T$_{cc}$). End values are given in paretheses for T$_{cc}$ and T$_{mp}$ also transition enthalpy, ΔH, is shown (J/g)

| n | T$_{gt}$ | ΔH | T$_{mp}$ | ΔH | T$_{cc}$ | ΔH |
|---|---|---|---|---|---|---|
| 0 | | | 107.5 (109.3) | 11.5 | 71.7 | −21.3 |
| 1 | | | 117.1 (119.2) | 48.0 | 84.6 | −61.1 |

TABLE 4-continued

Thermal data from DSC for chloroindate(III) salts. Transition temperatures (° C.) are measured from peak positions for glass transitions (T$_{gt}$), melting points (T$_{mp}$) and cold crystallization (T$_{cc}$). End values are given in paretheses for T$_{cc}$ and T$_{mp}$ also transition enthalpy, ΔH, is shown (J/g)

| n | T$_{gt}$ | ΔH | T$_{mp}$ | ΔH | T$_{cc}$ | ΔH |
|---|---|---|---|---|---|---|
| 2 | | | 29.1 (31.1) | 28.8 | 9.7 | −32.5 |
| 4 | −78.9 | 0.8 | −5.0 (−1.1) | 34.5 | | |
| 6 | −75.0 (−75.5) | 1.4 | | | | |
| 8 | −75.2 (−68.7) | 1.2 | | | | |
| 10 | −73.5 (−76.8) | 1.1 | −12.4 (−14.2) | 3.8 | | |
| 12 | | | 26.2 (29.8) | 77.5 | −46.4 | −22.8 |
| 14 | | | 31.2 (35.2) | 53.0 | −4.8 | −28.7 |
| 16 | | | 43.7 (45.5) | 94.8 | 20.0 | −89.8 |
| 18 | | | 61.3 (62.6) | 118.0 | 43.5 | −113.9 |

2.2.3 Viscosity Analyses

Figure 2:
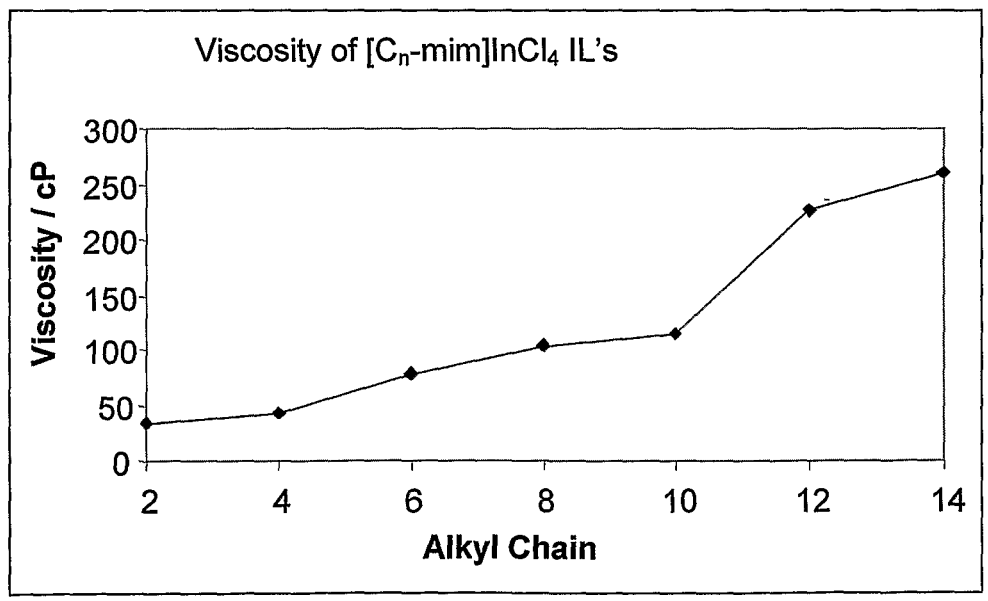
FIG. 2 shows viscosity as a function of chain length.

The viscosities of ionic liquids which were liquid at, or close to, ambient temperature were analysed with a viscometer. Salts that were measured were [C$_2$mim][InCl$_4$], [C$_4$mim][InCl$_4$], [C$_6$mim][InCl$_4$], [C$_8$mim][InCl$_4$], [C$_{10}$mim][InCl$_4$], [C$_{12}$mim][InCl$_4$] and [C$_{14}$mim][InCl$_4$]. The temperature in the measurements for salts with $C_n$: 4-14 was 20° C., but measurement of [C$_2$mim][InCl$_4$] was done at 25° C. Viscosity of ionic liquids increased when alkyl chain length was increased, as has been reported before with other imidazolium based ionic liquids. Viscosities of these chloroindate(III) ionic liquids are quite low, lower than viscosities with anions like Cl$^−$, PF$_6^−$ and BF$_4^−$. Low viscosity makes them also easier to handle. Results of the viscosity measurements are shown in FIG. 2.

2.3 Synthesis

2.3.1 1-Methylimidazolium chloroindate(III) [Hmim][InCl$_4$]

Indium(III)chloride (1.597 g, 7.2 mmol) was added to a round bottom flask containing 1-H-3-methylimidazolium chloride (0.85 g, 7.2 mmol). The mixture was heated with an oil bath until a homogeneous liquid was formed. The formed [Hmim][InCl$_4$] was dried under high vacuum. $^1$H-NMR (300 MHz, CD$_3$CN, ppm): δ 3.82 (6H, s, 2×NCH$_3$), 7.31 (1H, s, C(5)H), 7.32 (1H, s, C(4)H), 8.34 (1H, s, C(2)H. $^{13}$C-NMR (300 MHz, CD$_3$CN, ppm): δ 36.75 (NCH$_3$), 120.52 (C(5)H), 124.17 (C(4)H), 136.15 (C(2)H). Elemental analysis: Calculated: C, 14.14; H, 2.08; N, 8.25; Cl, 41.74; In, 33.80. Found: C, 13.42; H, 2.60; N, 7.32; Cl, 41.44; In, 33.41.

2.3.2 1,3-Dimethylimidazolium chloroindate(III) [C$_1$mim][InCl$_4$]

Indium(III)chloride (2.051 g, 9.3 mmol) was added to a round bottom flask containing 1,3-dimethylimidazolium chloride (1.230 g, 9.3 mmol). The mixture was heated with an oil bath until a homogeneous liquid was formed. The formed [C$_1$mim][InCl$_4$] was dried under high vacuum. $^1$H-NMR (300 MHz, CDCl$_3$, ppm): δ 1.63 (3H, t, J=7.5 Hz, CH$_3$), 4.03 (3H, s, NCH$_3$), 4.32 (2H, t, J=7.5 Hz, CH$_2$), 7.30 (1H, d, J=1.8 Hz, C(5)H), 7.31 (1H, d, J=1.8 Hz, C(4)H), 8.69 (1H, s, C(2)H. $^{13}$C-NMR (300 MHz, CDCl$_3$, ppm): δ 15.61 (CH$_3$), 37.19 (NCH$_3$), 45.75 (NCH$_2$), 122.49 (C(5)H), 124.13 (C(4) H), 134.85 (C(2)H). Elemental analysis: Calculated: C, 16.96; H, 2.56; N, 7.92; Cl, 32.46; In, 40.09. Found: C, 17.18; H, 2.71; N, 7.95; Cl, 32.35; In, 40.18.

2.3.3 1-Ethyl-3-methylimidazolium chloroindate(III) [C$_2$mim][InCl$_4$]

Indium(III)chloride (1.105 g, 5 mmol) was added to a round bottom flask containing 1-ethyl-3-methylimidazolium chloride (0.733 g, 5 mmol). The mixture was heated with an oil bath until a homogeneous liquid was formed. The formed [C$_2$mim][InCl$_4$] was dried under high vacuum. $^1$H-NMR (300 MHz, CDCl$_3$, ppm): δ 1.63 (3H, t, J=7.5 Hz, CH$_3$), 4.03 (3H, s, NCH$_3$), 4.32 (2H, t, J=7.5 Hz, CH$_2$), 7.30 (1H, d, J=1.8 Hz, C(5)H), 7.31 (1H, d, J=1.8 Hz, C(4)H), 8.69 (1H, s, C(2)H. $^{13}$C-NMR (300 MHz, CDCl$_3$, ppm): δ 15.61 (CH$_3$), 37.19 (NCH$_3$), 45.75 (NCH$_2$), 122.49 (C(5)H), 124.13 (C(4) H), 134.85 (C(2)H). Elemental analysis: Calculated: C, 20.04; H, 3.35; N, 7.80; Cl, 38.46; In, 30.70. Found: C, 19.59; H, 3.01; N, 7.52; Cl, 38.56; In, 31.22.

2.3.4 1-Butyl-3-methylimidazolium chloroindate(III) [C$_4$mim][InCl$_4$]

Indium(III)chloride (1.105 g, 5 mmol) was added to a round bottom flask containing 1-butyl-3-methylimidazolium chloride (0.873 g, 5 mmol). The mixture was heated with an oil bath until a homogeneous liquid was formed. The formed [C$_4$mim][InCl$_4$] was dried under high vacuum. $^1$H-NMR (300 MHz, CDCl$_3$, ppm): δ 1.00 (3H, t, J=7.5 Hz, CH$_3$), 1.42 (2H, m, J=7.5 Hz, NCH$_2$CH$_2$CH$_2$CH$_3$), 1.91 (2H, m, J=7.5 Hz, NCH$_2$CH$_2$CH$_2$CH$_3$), 4.01 (3H, s, NCH$_3$), 4.23 (2H, t, J=7.5 Hz, NCH$_2$CH$_2$CH$_2$CH$_3$), 7.31 (1H, d, J=1.8 Hz, C(5) H), 7.33 (1H, d, J=1.8 Hz, C(4)H), 8.58 (1H, s, C(2)H. $^{13}$C-NMR (300 MHz, CDCl$_3$, ppm): δ 13.17 (CH$_3$), 19.14 (CH$_2$), 31.54 (CH$_2$) 36.76 (NCH$_3$), 49.99 (NCH$_2$), 122.45 (C(5)H), 123.71 (C(4)H), 134.36 (C(2)H). Elemental analysis: Calculated: C, 24.20; H, 3.82; N, 7.18; Cl, 35.87; In, 2.50. Found: C, 24.27; H, 3.82; N, 7.08; Cl, 35.82; In, 29.01.

2.3.5 1-Hexyl-3-methylimidazolium chloroindate(III) [C$_6$mim][InCl$_4$]

Indium(III)chloride (3.150 g, 14 mmol) was added to a round bottom flask containing 1-hexyl-3-methylimidazolium chloride (2.900 g, 14 mmol). The mixture was heated with an oil bath until a homogeneous liquid was formed. The formed [C$_6$mim][InCl$_4$] was dried under high vacuum. $^1$H-NMR (300 MHz, CDCl$_3$, ppm): δ 0.89 (3H, t, J=7.0 Hz, CH$_3$), 1.33 (6H, m, CH$_2$), 1.91 (2H, m, J=7.5 Hz, NCH$_2$CH$_2$), 4.01 (3H, s, NCH$_3$), 4.22 (2H, t, J=7.5 Hz, NCH$_2$), 7.33 (1H, d, J=1.8 Hz, C(5)H), 7.35 (1H, d, J=1.8 Hz, C(4)H), 8.62 (1H, s, C(2)H. $^{13}$C-NMR (300 MHz, CDCl$_3$, ppm): δ 13.97 (CH$_3$), 22.32 (CH$_2$), 25.84 (CH$_2$), 29.98 (CH$_2$), 30.95 (CH$_2$), 37.09 (NCH$_3$), 50.60 (NCH$_2$), 122.64 (C(5)H), 124.02 (C(4)H), 134.97 (C(2)H). Elemental analysis: Calculated: C, 28.72; H, 4.57; N, 6.93; Cl, 32.69; In, 28.34. Found: C, 28.33; H, 4.52; N, 6.61; Cl, 33.45; In, 27.09.

2.3.6 1-Octyl-3-methylimidazolium chloroindate(III) [C$_8$mim][InCl$_4$]

Indium(III)chloride (0.707 g, 3.2 mmol) was added to a round bottom flask containing 1-octyl-3-methylimidazolium chloride (0.733 g, 3.2 mmol). The mixture was heated with an oil bath until a homogeneous liquid was formed. The formed [C$_8$mim][InCl$_4$] was dried under high vacuum. $^1$H-NMR (300 MHz, CDCl$_3$, ppm): δ 0.87 (3H, t, J=7.0 Hz, CH$_3$), 1.33 (10H, m, CH$_2$), 1.91 (2H, m, J=7.5 Hz, NCH$_2$CH$_2$), 4.00 (3H, s, NCH$_3$), 4.22 (2H, t, J=7.5 Hz, NCH$_2$), 7.35 (1H, d, J=1.8 Hz, C(5)H), 7.37 (1H, d, J=1.8 Hz, C(4)H), 8.57 (1H, s, C(2)H. $^{13}$C-NMR (300 MHz, CDCl$_3$, ppm): δ 14.06 (CH$_3$), 22.50 (CH$_2$), 26.15 (CH$_2$), 28.77 (CH$_2$), 28.88 (CH$_2$), 29.99 (CH$_2$), 31.57 (CH$_2$), 37.03 (NCH$_3$), 50.55 (NCH$_2$), 122.58 (C(5)H), 123.96 (C(4)H), 134.86 (C(2)H). Elemental analysis: Calculated: C, 32.15; H, 5.08; N, 6.1; Cl, 31.98; In, 26.85. Found: C, 31.89; H, 5.13; N, 6.20; Cl, 31.38; In, 25.40.

2.3.7 1-Decyl-3-methylimidazolium chloroindate(III) [C$_{10}$mim][InCl$_4$]

Indium(III)chloride (0.582 g, 2.6 mmol) was added to a round bottom flask containing 1-decyl-3-methylimidazolium chloride (0.678 g, 2.6 mmol). The mixture was heated with an oil bath until a homogeneous liquid was formed. The formed [C$_{10}$mim][InCl$_4$] was dried under high vacuum. $^1$H-NMR (300 MHz, CDCl$_3$, ppm): δ 0.88 (3H, t, J=7.0 Hz, CH$_3$), 1.33 (14H, m, CH$_2$), 1.91 (2H, m, J=7.2 Hz, NCH$_2$CH$_2$), 4.00 (3H, s, NCH$_3$), 4.21 (2H, t, J=7.5 Hz, NCH$_2$), 7.35 (1H, d, J=1.8 Hz, C(5)H), 7.37 (1H, d, J=1.8 Hz, C(4)H), 8.51 (1H, s, C(2)H. $^{13}$C-NMR (300 MHz, CDCl$_3$, ppm): δ 14.11 (CH$_3$), 22.61 (CH$_2$), 26.19 (CH$_2$), 28.85 (CH$_2$), 29.18 (CH$_2$), 29.27 (CH$_2$), 29.39 (CH$_2$), 30.01 (CH$_2$), 31.79 (CH$_2$), 37.07 (NCH$_3$), 50.61 (NCH$_2$), 122.64 (C(5)H), 124.02 (C(4)H), 134.76 (C(2)H). Elemental analysis: Calculated: C, 35.08; H, 5.36; N, 5.80; Cl, 29.76; In, 24.18. Found: C, 35.03; H, 5.67; N, 5.84; Cl, 29.54; In, 23.92.

2.3.8 1-Dodecyl-3-methylimidazolium chloroindate(III) [Cl$_2$mim][InCl$_4$]

Indium(III)chloride (0.453 g, 2.1 mmol) was added to a round bottom flask containing 1-dodecyl-3-methylimidazolium chloride (0.587 g, 2.1 mmol). The mixture was heated with an oil bath until a homogeneous liquid was formed. The formed [C₁₂mim][InCl₄] was dried under high vacuum. ¹H-NMR (300 MHz, CDCl₃, ppm): δ 0.88 (3H, t, J=7.0 Hz, CH₃), 1.33 (18H, m, CH₂), 1.91 (2H, m, J=7.2 Hz, NCH₂CH₂), 4.00 (3H, s, NCH₃), 4.21 (2H, t, J=7.5 Hz, NCH₂), 7.34 (1H, d, J=1.8 Hz, C(5)H), 7.36 (1H, d, J=1.8 Hz, C(4)H), 8.58 (1H, s, C(2)H. ¹³C-NMR (300 MHz, CDCl₃, ppm): δ 14.18 (CH₃), 22.72 (CH₂), 26.31 (CH₂), 28.97 (CH₂), 29.39 (2×CH₂), 29.55 (CH₂), 29.64 (2×CH₂), 30.12 (CH₂), 31.95 (CH₂), 37.16 (NCH₃), 50.70 (NCH₂), 122.65 (C(5)H), 124.07 (C(4)H), 135.04 (C(2)H). Elemental analysis: Calculated: C, 38.03; H, 5.76; N, 5.56; Cl, 28.8; In, 22.72. Found: C, 37.82; H, 6.15; N, 5.51; Cl, 27.91; In, 22.60.

2.3.9 1-Methyl-3-tetradecylimidazolium chloroindate(III) [C₁₄mim][InCl₄]

Indium(III)chloride (0.388 g, 1.8 mmol) was added to a round bottom flask containing 1-tetradecyl-3-methylimidazolium chloride (0.553 g, 1.8 mmol). The mixture was heated with an oil bath until a homogeneous liquid was formed. The formed [C₁₄mim][InCl₄] was dried under high vacuum. ¹H-NMR (300 MHz, CDCl₃, ppm): δ 0.88 (3H, t, J=7.0 Hz, CH₃), 1.33 (22H, m, CH₂), 1.91 (2H, m, J=7.2 Hz, NCH₂CH₂), 4.00 (3H, s, NCH₃), 4.20 (2H, t, J=7.5 Hz, NCH₂), 7.33 (1H, d, J=1.8 Hz, C(5)H), 7.35 (1H, d, J=1.8 Hz, C(4)H), 8.54 (1H, s, C(2)H. ¹³C-NMR (300 MHz, CDCl₃, ppm): δ 14.23 (CH₃), 22.78 (CH₂), 26.37 (CH₂), 29.02 (CH₂), 29.44 (3×CH₂), 29.60 (CH₂), 29.70 (3×CH₂), 30.17 (CH₂), 32.00 (CH₂), 37.23 (NCH₃), 50.78 (NCH₂), 122.68 (C(5)H), 124.11 (C(4)H), 135.12 (C(2)H). Elemental analysis: Calculated: C, 40.79; H, 6.49; N, 5.23; Cl, 26.08; In, 2.18. Found: C, 40.33; H, 6.58; N, 5.23; Cl, 26.45; In, 21.42.

2.3.10 1-Hexadecyl-3-methylimidazolium chloroindate(III) [C₁₆mim][InCl₄]

Indium(III)chloride (0.264 g, 1.2 mmol) was added to a round bottom flask containing 1-hexadecyl-3-methylimidazolium chloride (0.418 g, 1.2 mmol). The mixture was heated with an oil bath until a homogeneous liquid was formed. The formed [C₁₆mim][InCl₄] was dried under high vacuum. ¹H-NMR (300 MHz, CDCl₃, ppm): δ 0.88 (3H, t, J=7.0 Hz, CH₃), 1.33 (26H, m, CH₂), 1.91 (2H, m, J=7.2 Hz, NCH₂CH₂), 4.00 (3H, s, NCH₃), 4.22 (2H, t, J=7.5 Hz, NCH₂), 7.32 (1H, d, J=1.8 Hz, C(5)H), 7.36 (1H, d, J=1.8 Hz, C(4)H), 8.62 (1H, s, C(2)H. ¹³C-NMR (300 MHz, CDCl₃, ppm): δ 14.22 (CH₃), 22.77 (CH₂), 26.36 (CH₂), 29.03 (CH₂), 29.45 (2×CH₂), 29.62 (CH₂), 29.76 (6×CH₂), 30.18 (CH₂), 32.00 (CH₂), 37.21 (NCH₃), 50.72 (NCH₂), 122.62 (C(5)H), 124.08 (C(4)H), 135.20 (C(2)H). Elemental analysis: Calculated: C, 42.50; H, 6.62; N, 5.07; Cl, 24.81; In, 20.04. Found: C, 42.58; H, 6.97; N, 4.97; Cl, 25.14; In, 20.35.

2.3.11 1-Methyl-3-octadecylimidazolium chloroindate(III) [C₁₈mim][InCl₄]

Indium(III)chloride (0.287 g, 1.3 mmol) was added to a round bottom flask containing 1-octyl-3-methylimidazolium chloride (0.481 g, 1.3 mmol). The mixture was heated with an oil bath until a homogeneous liquid was formed. The formed [C₁₈mim][InCl₄] was dried under high vacuum. ¹H-NMR (300 MHz, CDCl₃, ppm): δ 0.88 (3H, t, J=7.0 Hz, CH₃), 1.34 (22H, m, CH₂), 1.91 (2H, m, J=7.2 Hz, NCH₂CH₂), 4.00 (3H, s, NCH₃), 4.21 (2H, t, J=7.5 Hz, NCH₂), 7.33 (1H, d, J=1.8 Hz, C(5)H), 7.35 (1H, d, J=1.8 Hz, C(4)H), 8.53 (1H, s, C(2)H. ¹³C-NMR (300 MHz, CDCl₃, ppm): δ 14.22 (CH₃), 22.78 (CH₂), 26.36 (CH₂), 29.02 (CH₂), 29.45 (2×CH₂), 29.62 (CH₂), 29.80 (8×CH₂), 30.15 (CH₂), 32.01 (CH₂), 37.23 (NCH₃), 50.78 (NCH₂), 122.71 (C(5)H), 124.14 (C(4)H), 135.00 (C(2)H). Elemental analysis: Calculated: C, 44.46; H, 6.91; N, 4.53; Cl, 23.16; In, 20.03. Found: C, 44.62; H, 7.32; N, 4.73; Cl, 23.95; In, 19.39.

2.3.12 Methylimidazolium Chloroindate (III) [Hmim][InCl₄]

Figure 22:
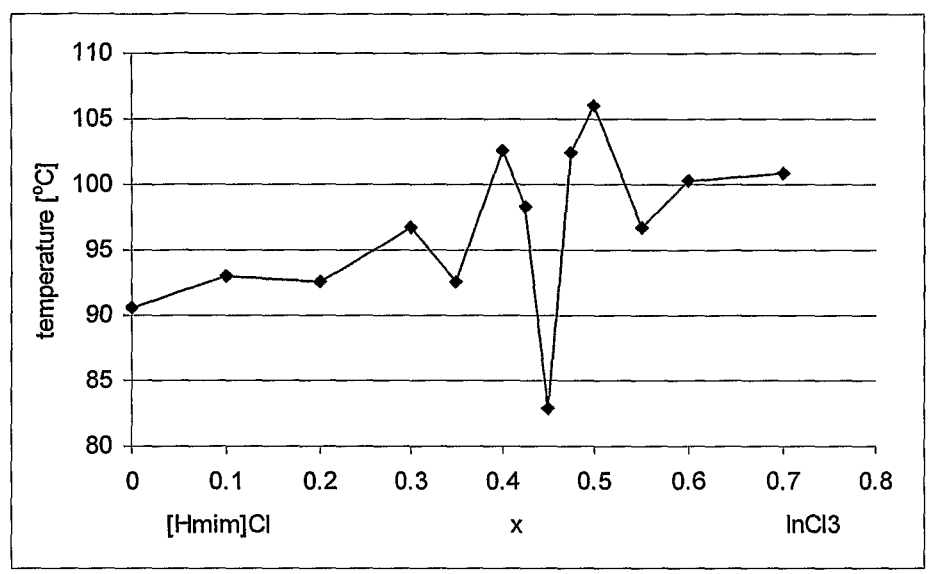
FIG. 22 shows melting points of [Hmim]Cl:InCl$_3$ for various values of x(InCl$_3$).

A range of ionic liquids having an InCl₃ mole fraction x=0.1, 0.2, 0.3, 0.35, 0.4, 0.425, 0.45, 0.475, 0.5, 0.55, 0.6, 0.7 were prepared. [Hmim]Cl (FW=118.566) and InCl₃ were dried in a high vacuum for 24 hours. The compounds were then combined and heated until they liquified. The resulting compound was carefully transferred to a desiccator filled with dry nitrogen. DSC analysis results are shown in FIG. 22.

3. PHASE DIAGRAMS OF [C₂mim]Cl+InCl₃

The thermal behaviour of mixtures of [C₂mim]Cl+InCl₃ was studied in detail. The mixtures were prepared from dried [C₂mim]Cl and InCl₃. InCl₃ was added in small batches into [C₂mim]Cl (2.6 g, 0.0177 mol). The mixture was heated with an oil bath until a homogeneous liquid or mixture was formed. After cooling to room temperature the mixture was analysed using a differential scanning calorimeter (DSC). The whole phase diagram was measured two times. The first time (Run 1) the following compositions, in which the InCl₃ mole fraction x(InCl₃) was ca. 0, 0.5, 0.10, 0.15, 0.20, 0.225, 0.25, 0.275, 0.30, 0.325, 0.35, 0.375, 0.40, 0.425, 0.45, 0.475, 0.50, 0.525, 0.55, 0.575, 0.60, 0.625, 0.65, 0.675, 0.70 and 0.75 were analysed with DSC. The second time (Run 2) the analysis was started from composition x(InCl₃)=0.15 and the next sample contained 0.20 mol % of InCl₃. Then samples were analysed with DSC after every 1% addition of InCl₃ until the amount of InCl₃ was 65 mol %. Each sample was analysed with three heating and two cooling cycles. Glass transitions and melting points were usually determined from the peak positions for the second heating cycle. Results were quite well reproducible.

3.1 First DSC analysis, Run 1

Figure 3:
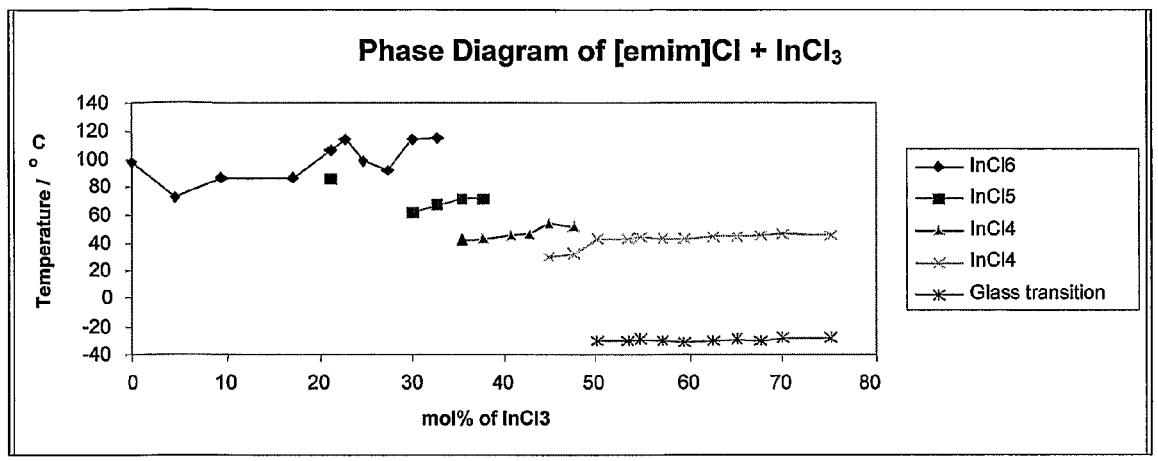
FIG. 3 shows a phase diagram for salts of the present invention as a function of $InCl_3$ concentration (Run 1)

In this analysis the purity of InCl₃ was 99.9%. The melting points and glass transitions temperatures were mainly determined by Perkin-Elmer Pyris 1 DSC (analysis could be started from −100° C.). Samples where the amount of x(InCl₃) was 0.211, 0.247 and 0.273 were measured with Perkin-Elmer Pyris 7 DSC (analysis had to be started at 25° C.). Analysis with these two machines gave slightly different results. The melting points and glass transition temperatures are shown in Table 5 below, and the phase diagram is shown in FIG. 3. There it can be seen that the results obtained from analysis with Pyris 7 are not in line with results from analysis with Pyris 1. The melting points from analysis with Pyris 7 are on the low side. This first measurement of the phase diagram were used as a guide to the next and more detailed measurement, Run 2. When more InCl₃ was added into [C₂mim]Cl its DSC trace became more and more complicated. This is possibly due to the first peak, which corresponds to the anion InCl₆⁻, second peak to InCl₅⁻, peak around 40° C. to InCl₄⁻ and lowest peak is the glass transition.

TABLE 5

Melting points and glass transitions (T$_{gt}$) of [C$_2$mim]Cl + InCl$_3$ from analysis Run 1.

| Code | Mol % | InCl$_6$ (° C.) | InCl$_5$ (° C.) | InCl$_4$ (° C.) | InCl$_4$ (° C.) | T$_{gt}$ (° C.) |
|---|---|---|---|---|---|---|
|   | 0     | 97.2  |      |      |      |       |
| a | 4.6   | 72.5  |      |      |      |       |
| b | 9.5   | 86.4  |      |      |      |       |
| c | 17    | 86.8  |      |      |      |       |
| d | 21.2[a] | 106 | 86  |      |      |       |
| e | 22.7  | 114.2 |      |      |      |       |
| f | 24.6[a] | 98.5 |      |      |      |       |
| g | 27.3[a] | 92   |      |      |      |       |
| h | 30.1  | 114.2 | 61.6 |      |      |       |
| i | 32.8  | 114.4 | 67.4 |      |      |       |
| j | 35.5  |       | 71.6 | 42.2 |      |       |
| k | 37.7  |       | 71.6 | 42.7 |      |       |
| l | 40.9  |       |      | 44.7 |      |       |
| m | 42.8  |       |      | 46.1 |      |       |
| n | 44.9  |       |      | 54.2 | 30.2 |       |
| o | 47.6  |       |      | 51.6 | 31.9 |       |
| P | 50.2  |       |      |      | 42.5 | −30.6 |
| q | 53.5  |       |      |      | 43.4 | −30.4 |
| r | 54.9  |       |      |      | 44.5 | −29.6 |
| s | 57.2  |       |      |      | 42.6 | −30.6 |
| t | 59.5  |       |      |      | 42.7 | −30.8 |
| u | 62.5  |       |      |      | 44   | −30.6 |
| v | 65    |       |      |      | 43.7 | −28.8 |
| w | 67.6  |       |      |      | 45.2 | −29.9 |
| x | 69.9  |       |      |      | 45.9 | −27.6 |
| y | 75.1  |       |      |      | 45.2 | −28.3 |

[a]sample was analysed with Pyris 7.

3.2 Second DSC Analysis, Run 2

Figure 4:
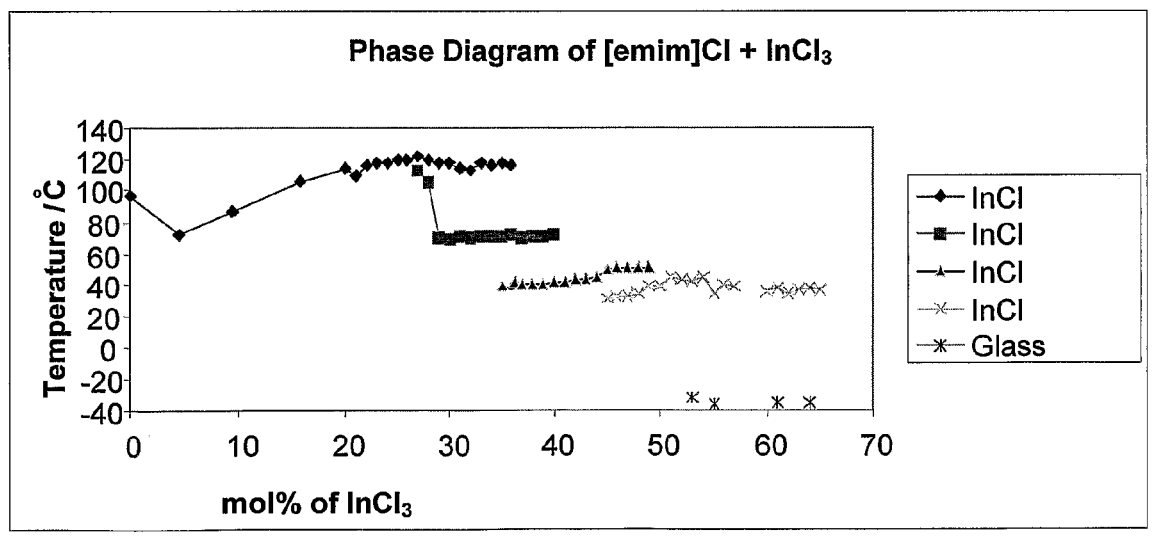
FIG. 4 shows a phase diagram for salts of the present invention as a function of $InCl_3$ concentration (Run 2)

In this analysis the purity of InCl$_3$ was 98%. The melting points and glass transition temperatures were determined only using a Perkin-Elmer Pyris 1 DSC and the same method was used as in previous analysis, Run 1. The phase diagram is shown in FIG. 4. When the amount of InCl$_3$ was between 0.20-0.26 only one transition was seen and a peak appeared around 115° C. When more InCl$_3$ was added another transition was seen in the DSC trace and had a lower melting point. At the same time the higher peak started to move downwards and became steadily smaller until it disappeared. When the amount of InCl$_3$ was just below 0.40. The other peak which was first seen when amount of InCl$_3$ was 0.27 also started to move downwards from 112° C. to 70° C. This peak stayed at this temperature, 70° C., even when the amount of InCl$_3$ was above 0.30 and its peak gradually decreased until it disappeared when amount of InCl$_3$ was around 0.40. Third transition was seen when amount of InCl$_3$ was 0.35 and the peak appeared around 40° C. This peak moved upwards when more InCl$_3$ was added. When the amount of InCl$_3$ was 0.45 a peak appeared at 50° C. and another peak was seen next to it at 30° C. The peak at 50° C. became smaller and the peak at 30° C. became bigger and was also moving upwards. When the amount of InCl$_3$ was 0.50 there was only one peak around 40° C. This peak was seen at the same place when more InCl$_3$ was added and also glass transition was seen quite often around −30° C. InCl$_3$ was added into the mixture until its amount was 0.65. All observed transitions are shown in Table 6 below.

TABLE 6

Melting points and glass transitions (T$_{gt}$) of [C$_2$mim]Cl + InCl$_3$ from analysis Run 2.

| mol % | InCl$_6$ | InCl$_5$ (° C.) | InCl$_5$ (° C.) | InCl$_4$ (° C.) | T$_{gt}$ (° C.) |
|---|---|---|---|---|---|
| 0    | 97.2  |       |       |      |   |
| 4.6  | 72.5  |       |       |      |   |
| 9.5  | 86.4  |       |       |      |   |
| 15.7 | 106.5 |       |       |      |   |
| 20   | 114.2 |       |       |      |   |
| 21   | 109.7 |       |       |      |   |
| 22   | 116.4 |       |       |      |   |
| 23   | 117.6 |       |       |      |   |
| 24   | 117.1 |       |       |      |   |
| 25   | 120.1 |       |       |      |   |
| 26   | 119.8 |       |       |      |   |
| 27   | 121.8 | 112.9 |       |      |   |
| 28   | 119.4 | 104.7 |       |      |   |
| 29   | 116.8 | 70.3  |       |      |   |
| 30   | 116.9 | 68.8  |       |      |   |
| 31   | 113.9 | 71    |       |      |   |
| 32   | 112.9 | 69.6  |       |      |   |
| 33   | 116.8 | 70.5  |       |      |   |
| 34   | 116.6 | 71.2  |       |      |   |
| 35   | 117.1 | 71.3  |       | 39.6 |   |
| 36   | 116.1 | 71.7  |       | 37.1 |   |
| 37   |       | 70.1  |       | 40.2 |   |
| 38   |       | 70.9  |       | 39.9 |   |
| 39   |       | 71.3  |       | 40.4 |   |
| 40   |       | 71.8  |       | 42   |   |
| 41   |       |       |       | 41.8 |   |
| 42   |       |       |       | 44.1 |   |
| 43   |       |       |       | 44.3 |   |
| 44   |       |       |       | 44.6 |   |
| 45   |       |       |       | 49.8 | 31.5 |
| 46   |       |       |       | 50.9 | 32.9 |
| 47   |       |       |       | 50.7 | 32.7 |
| 48   |       |       |       | 50.2 | 34.7 |
| 49   |       |       |       | 50.2 | 39.3 |
| 50   |       |       |       |      | 39.4 |
| 51   |       |       |       |      | 45.3 |
| 52   |       |       |       |      | 44.2 |

TABLE 6-continued

Melting points and glass transitions ($T_{gt}$) of [C$_2$mim]Cl + InCl$_3$ from analysis Run 2.

| mol % | InCl$_6$ | InCl$_5$ (° C.) | InCl$_5$ (° C.) | InCl$_4$ (° C.) | $T_{gt}$ (° C.) |
|---|---|---|---|---|---|
| 53 | | | | 42.2 | −31.6 |
| 54 | | | | 44.6 | |
| 55 | | | | 34.9 | −36.1 |
| 56 | | | | 40.7 | |
| 57 | | | | 39.2 | |
| 60 | | | | 36.2 | |
| 61 | | | | 37.9 | −35.8 |
| 62 | | | | 35.2 | |
| 63 | | | | 36.6 | |
| 64 | | | | 38 | −36 |
| 65 | | | | 37.1 | |

3.3 Comparison between Analyses of Run 1 and Run 2

DSC traces of samples where the amount of InCl$_3$ was x(InCl$_3$) 0.23, 0.25, 0.33, 0.5, 0.55, 0.6 and 0.65 were compared between Run 1 and Run 2. When x(InCl$_3$) is 0.25 there should be only one kind of ionic liquid/salt in a mixture and that is [C$_2$mim]$_3$[InCl$_6$]. When x(InCl$_3$) is 0.33 there should be only [C$_2$mim]InCl$_5$ in a mixture and when x(InCl$_3$) is 0.50 there should be only [C$_2$mim]InCl$_4$ in a mixture. The results of DSC have been compared. The first value is from the analysis of Run 1 and the second value is from Run 2. When x(InCl$_3$) was 0.23 melting points were at 114° C. and 117° C., respectively. When x(InCl$_3$) was 0.25 melting points were at 98° C. and 120° C., respectively. Run 1 was analysed with Pyris 7 and the melting point appeared too low. All samples with x(InCl$_3$)<0.27 showed only one peak for transition. When x(InCl$_3$) was 0.33 transitions were seen at 114° C. and 67° C.; and at 117° C., 71° C. and 61° C., respectively. The DSC trace of Run 2 was more complicated than Run 1. The melting points were at 113° C. and 70° C. for 0.32 and 117° C. and 71° C. for 0.34. There is one extra peak on DSC trace of Run 2, x(InCl$_3$)=0.33. When x(InCl$_3$) was 0.50 also the glass transition was seen in addition of melting point. Glass transition was at −30° C. and melting point at 42° C. for Run 1 and in Run 2 only one peak was seen clearly and this was the melting point at 44° C. When amount of InCl$_3$ exceeds the amount of [C$_2$mim]Cl, x(InCl$_3$)>0.50, there were no difference between DSC traces from both analysis. They were all the same from x(InCl$_3$)=0.55 to 0.75. But values from analysis of Run 2 were some what lower than from analysis of Run 1. When x(InCl$_3$) was 0.55 transition points were 45° C. and −30° C. for Run 1 and 35° C. and −36° C. for Run 2. When x(InCl$_3$) was 0.60 transition points were 43° C. and −30° C.; and at 36° C., respectively. When x(InCl$_3$) was 0.65 transition points were 43° C. and −31° C.; and at 35° C., respectively. For the DSC traces of 0.67 and 0.75 from Run 1 the transitions were 43° C., −29° C.; and 44° C. and −29° C., respectively. The glass transition was easier to see from analysis of Run 1. The reason why melting points and transition points were lower in Run 2 than Run 1 may correlate with the amount of water in a mixture. Samples which contain x(InCl$_3$)>0.54 were analysed couple of weeks later than all previous samples. Some of the samples were dried in a high vacuum and they were analysed again, but this didn't change the melting point.

Figure 5:
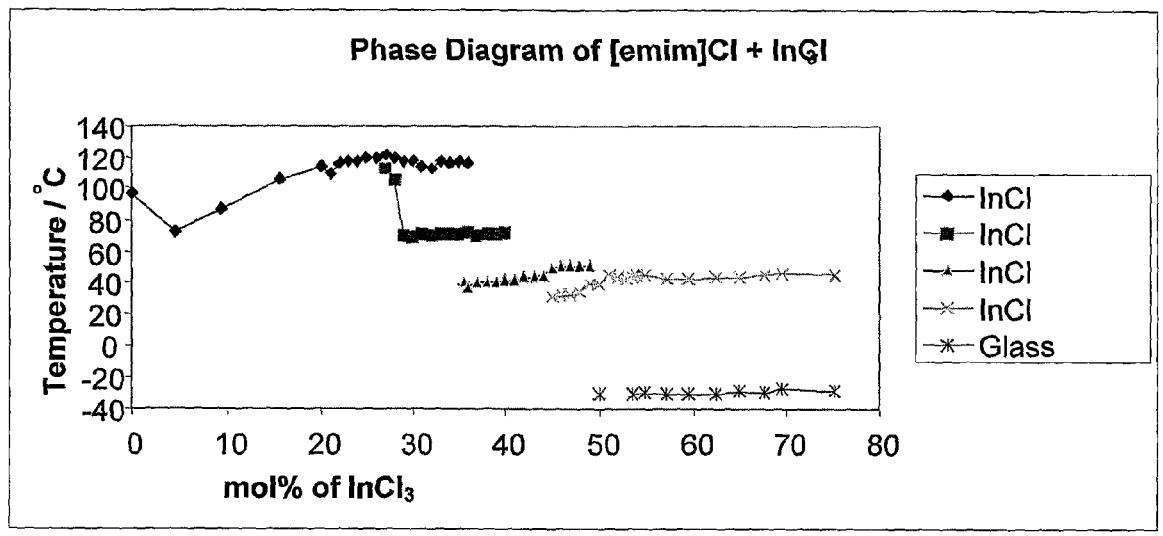
FIG. 5 shows a phase diagram for salts of the present invention as a function of $InCl_3$ concentration (Runs 1 and 2)

FIG. 5 shows a phase diagram for data points from both analyses. Values of transition points below x(InCl$_3$)=0.15 and above 0.55 are from analysis of Run 1 and values between 0.15 and 0.54 are from analysis of Run 2. The reason for this is that it is thought that the values above 0.54 from analysis Run 2 are not accurate and somewhat too low.

3.4 Microscopic Analysis

The following [C$_2$mim]Cl+InCl$_3$ mixtures, x(InCl$_3$)=0.25, 0.33, 0.5, 0.55, 0.6 and 0.65 were also analysed using a microscope. Samples were first heated at rate 10° C./min and then cooled down at the same rate. A second time the same sample was heated at a rate of 1° C./min. Melting of the mixture was observed both times, but slower heating gives more exact values for melting points. Only one transition was seen with a mixture of 0.25 and this melting point was 105-108° C. When a mixture of 0.33 was heated several melting points were seen. First was around 40° C., second was around 70° C. and third was around 110° C. For a mixture of 0.5 melting point was at 33-36° C. and then the whole mixture was liquid. The mixtures of [C$_2$mim]Cl+InCl$_3$, where x(InCl$_3$) was 0.55, 0.6 and 0.65 all behaved similar ways. The melting point was seen at 33-36° C. but some hexagonal crystals didn't melt at this temperature. The excess of InCl$_3$ will not dissolve into [C$_2$mim]Cl+InCl$_3$ mixture. These InCl$_3$ crystals were seen even if the sample was heated up to 350° C. Mixture seems to be stable up to 250° C. but after that it will decompose.

3.5 Conclusions

The results from DSC and microscopic analysis are similar. The melting points are some what lower in the microscopic analysis, because the heating rate was slower, 1° C./min. With the DSC analysis the used heating and cooling rate was 10° C./min. The [C$_2$mim]Cl+InCl$_3$ mixture with x(InCl$_3$)=0.33 is the most complicated of these different mixtures and that's why several transitions are seen. The composition of formula x(InCl$_3$) which will form some crystals is x(InCl$_3$) 0.25. This composition is simplest of these three and it has highest melting point, above 100° C., which makes it easiest to recrystallise.

4. PREPARATION OF ALKYLPYRIDINIUM AND ALKYLPYRROLIDINE CHLORIDES

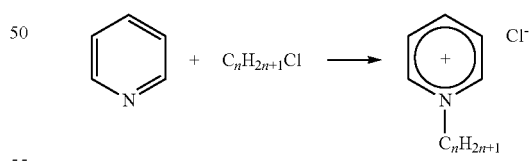

n = 4, 6, 8 ... 18

4.1 General Synthesis

[C$_n$-pyr]Cl (n=4, 6, 8, 10, 12, 14, 16 and 18) was prepared from 1 equivalent of pyridine and corresponding 1:1 equivalent of alkyl chloride at 95° C. under a nitrogen atmosphere. The compounds were washed both with hexane/cyclohexane and ethyl acetate to remove excess alkyl chloride. The reaction times and their states are shown in Table 7 below.

Approximately 40 grams of product was obtained.

TABLE 7

Preparation of [C$_n$-pyr]Cl

| Compounds studied | Reaction times/days | State | Colour |
|---|---|---|---|
| [C$_4$py] Cl | 4 | Solid | white |
| [C$_6$py] Cl | 5 | Solid | black |
| [C$_8$py] Cl | 6 | liquid | Amber brown |
| [C$_{10}$py] Cl | 5 | solid | Toffee, light brown |
| [C$_{12}$py] Cl | 9 | solid | Yellow brown |
| [C$_{14}$py] Cl | 14 | solid | Brown |
| [C$_{16}$py] Cl | 10 | solid | Dark brown |
| [C$_{18}$py] Cl | 10 | solid | Medium brown |

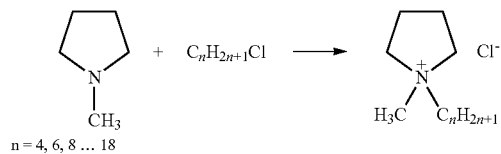

n = 4, 6, 8 ... 18

[C$_n$Mepyrrolid]Cl (n=4, 6, 8, 10, 12, 14, 16 and 18) was prepared from 1 equivalent of methylpyrrolidine and a 1:1 equivalent of alkyl chloride at 95° C. under a nitrogen atmosphere. The compounds were washed both with hexane/cyclohexane and ethyl acetate to remove excess alkyl chloride. The reaction times and their states are given in the Table 8 below.

As above, approximately 40 g of product was obtained.

TABLE 8

Preparation of [C$_n$Mepyrrolid]Cl

| Compounds studied | Reaction times | State | Colour |
|---|---|---|---|
| [C$_4$Mepyrrolid] Cl | 26 hours | Solid | white |
| [C$_6$Mepyrrolid] Cl | 53 hours | Solid | Yellow |
| [C$_8$Mepyrrolid] Cl | 42 hours | Solid | Beige |
| [C$_{10}$Mepyrrolid] Cl | 45 hours | solid | Toffee, light brown |
| [C$_{12}$Mepyrrolid] Cl | 27 hours | solid | Pale Yellow |
| [C$_{14}$Mepyrrolid] Cl | 6 days | solid | Brown |
| [C$_{16}$Mepyrrolid] Cl | 3 days | solid | Light brown |
| [C$_{18}$Mepyrrolid] Cl | 3 days | solid | Dark brown |

4.2 Analysis

The melting points of [C$_n$pyr]Cl and [C$_n$Mepyrrolid]Cl were observed and are shown in Table 9 below.

TABLE 9

The melting points of [C$_n$pyr]Cl and [C$_n$Mepyrrolid]Cl

| Compounds studied | Melting points/° C. |
|---|---|
| [C$_4$py] Cl | 130 |
| [C$_6$py] Cl | 41 |
| [C$_8$py] Cl | liquid |
| [C$_{10}$py] Cl | 43 |
| [C$_{12}$py] Cl | 62 |
| [C$_{14}$py] Cl | 78 |
| [C$_{16}$py] Cl | 86 |
| [C$_{18}$py] Cl | 88 |
| [C$_4$Mepyrrolid] Cl | 202 |
| [C$_6$Mepyrrolid] Cl | 188 |

TABLE 9-continued

The melting points of [C$_n$pyr]Cl and [C$_n$Mepyrrolid]Cl

| Compounds studied | Melting points/° C. |
|---|---|
| [C$_8$Mepyrrolid] Cl | 183.5 |
| [C$_{10}$Mepyrrolid] Cl | 174 |
| [C$_{12}$Mepyrrolid] Cl | 184 |
| [C$_{14}$Mepyrrolid] Cl | 195 |
| [C$_{16}$Mepyrrolid] Cl | 199 |
| [C$_{18}$Mepyrrolid] Cl | 214 |

It can be seen that [C$_n$Mepyrrolid]Cls generally have higher melting points than [C$_n$py]Cl with identical side chains.

4.3 Preparation of Chloroindate (III) Salts 4.3.1 [(C$_6$H$_{13}$)$_3$C$_{14}$H$_{29}$P][InCl$_4$]

Figure 12:
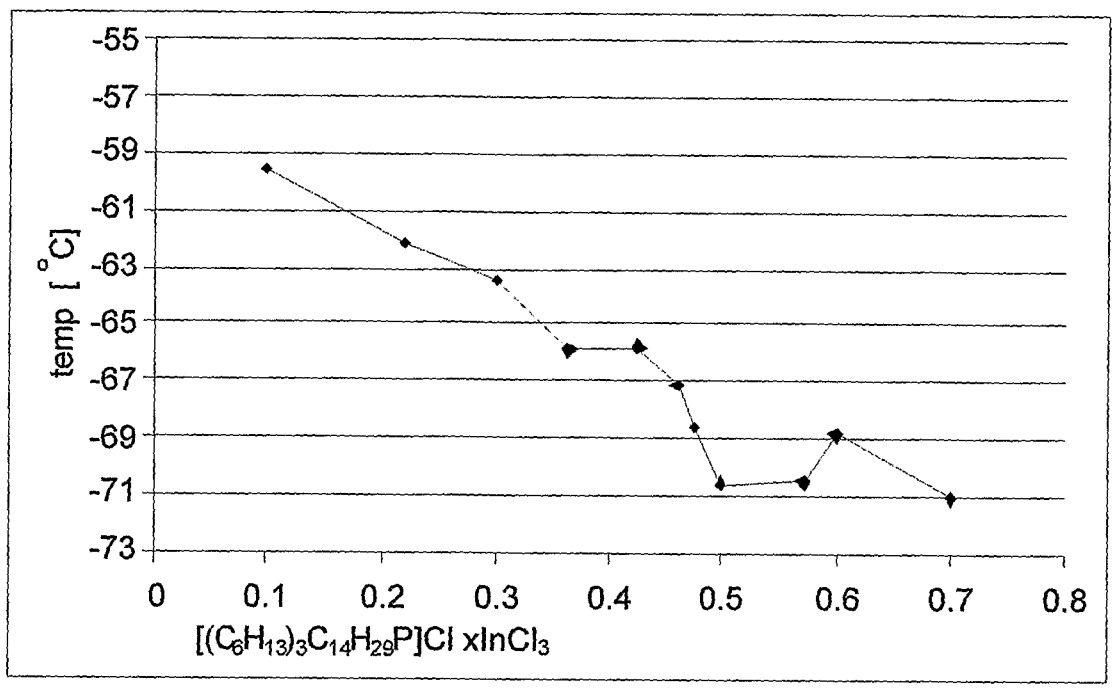
FIG. 12 shows the melting points of [(C$_6$H$_{13}$)$_3$C$_{14}$H$_{29}$P]Cl:InCl$_3$ for various values of x(InCl$_3$)

A range of ionic liquids with a InCl$_3$ mole fraction x(InCl$_3$)=0.1, 0.2, 0.3, 0.35, 0.4, 0.425, 0.45, 0.475, 0.5, 0.55, 0.6, 0.7 were prepared. [(C$_6$H$_{13}$)$_3$C$_{14}$H$_{29}$P]Cl (MW=519.322) and InCl$_3$ were separately dried in high vacuum for 24 hours. After drying, the compounds were added together and heated until they liquified. The resulting compound was carefully transferred to a desiccator filled with dry nitrogen. DSC analysis was taken (see FIG. 12).

4.3.2 [C$_4$Mepyrrolid][InCl$_4$]

Figure 13:
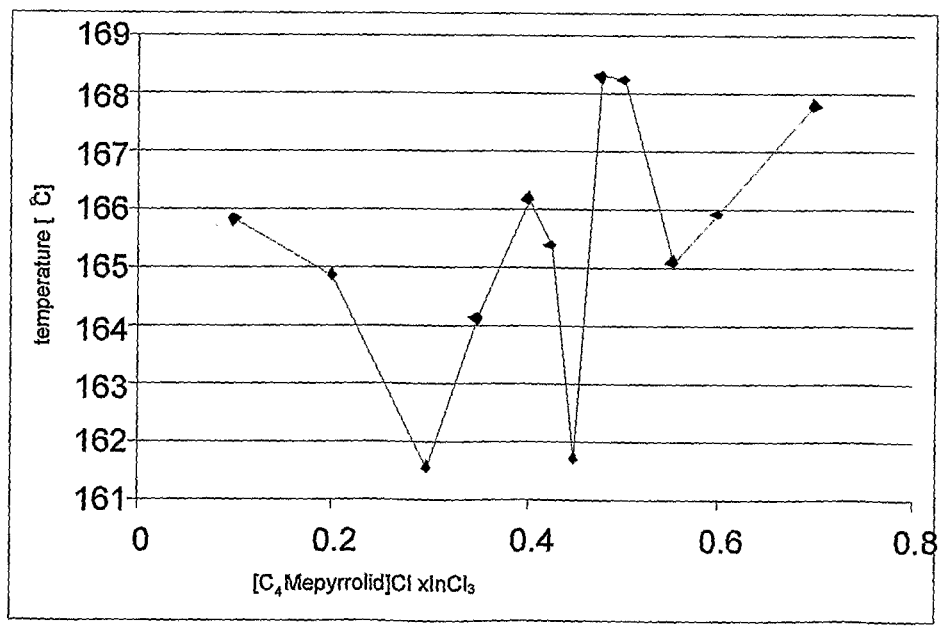
FIG. 13 shows the melting points of [C$_4$Mepyrrolid]Cl:InCl$_3$ for various values of x(InCl$_3$)

A range of ionic liquids with a InCl$_3$ mole fraction x(InCl$_3$)=0.1, 0.2, 0.3, 0.35, 0.4, 0.425, 0.45, 0.475, 0.5, 0.55, 0.6, 0.7 were prepared. [C$_4$Mepyrrolid]Cl (FW=177.718) and InCl$_3$ were separately dried in high vacuum for 24 hours. After drying the compounds were combined and heated until they liquified. The resulting compound was carefully transferred to the desiccator filled with dry nitrogen. DSC analysis is shown in FIG. 13.

4.3.3 [C$_8$py][InCl$_4$]

Figure 14:
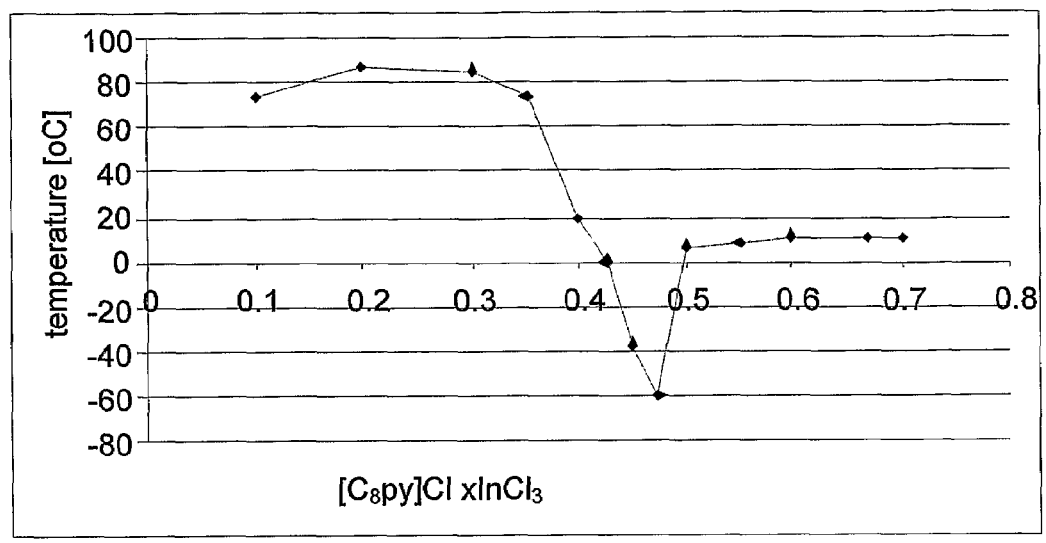
FIG. 14 shows the melting points of [C$_8$py]Cl:InCl$_3$ for various values of x(InCl$_3$)

A range of ionic liquids with a InCl$_3$ mole fraction x(InCl$_3$)=0.1, 0.2, 0.3, 0.35, 0.4, 0.425, 0.45, 0.475, 0.5, 0.55, 0.6, 0.7 were prepared. [C$_8$py]Cl (FW=239.789) and InCl$_3$ were dried separately in a high vacuum for 24 hours. After drying, the compounds were combined and heated until they liquified. The resulting compound was carefully transferred to a desiccator filled with dry nitrogen. DSC analysis is shown in FIG. 14.

Dimerisation Reactions of Isobutene

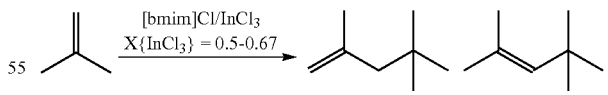

Due to the nature of the reaction, oligomers such as tri-, tetra-, penta-, hexa-, hepta- and octamers are also produced. By changing the reaction conditions, for example the ionic liquid, its composition, temperature, reaction time and reaction set up, it is possible to control the product distribution. The general reaction is to mix a catalytic amount of ionic liquid with the gaseous starting material and when products are formed they will form a liquid layer above the ionic liquid.

The ionic liquid used in this reaction was 1-butyl-3-methylimidazole chloroindate(III). This kind of ionic liquid works as a solvent and as a catalyst. [C$_4$mim]InCl$_4$ was also chosen because it is liquid at room temperature and because products won't dissolve into the products of the reaction.

A first reaction was carried in an autoclave and different compositions of ionic liquids were used as a catalytic solvent. The amount of InCl$_3$ in IL was x(InCl$_3$)=0.50, 0.52, 0.55, 0.57, 0.58, 0.6 and 0.66. The composition of the ionic liquid will affect the product distribution and the temperature which is needed to make the reaction to happen. Different reaction set ups were tested with two different ionic liquids x(InCl$_3$)= 0.58 and 0.55 and at different reaction temperatures. In the first reactions in an autoclave isobutene was added as a single batch and in later reactions, with modified reactors, it was fed continuously into a reactor usually at rate 1 cm$^3$/min. Products were analysed with GCMS and also NMR. The GC graphs were integrated manually and product compositions are given as percentages of di-, tri-, tetra-, penta-, hexa-, hepta- and octamers formed.

4.1 Oligomerisations in IL with composition x(InCl$_3$)=0.5-0.67

These reactions were carried in a glass reactor (200 ml, autoclave) equipped with magnetic stirring bar. Reactions were done in seven different composition of 1-butyl-3-methylimidazole chloro(III)indate (IL). The amount of InCl$_3$ in the IL was x(InCl$_3$)=0.5, 0.52, 0.55, 0.57, 0.58, 0.6 and 0.66. Ionic liquid with the desired InCl$_3$ content, x(InCl$_3$)=0.5-0.67, was prepared prior by reaction of [C$_4$mim]Cl and InCl$_3$. It was usually dried in a high vacuum before use and 1 g of it was weighted into a reactor. After that the reactor was flushed with gaseous starting material, isobutene. In the beginning of the reaction the gas pressure was about 1.2 bar and it decreased when reaction proceeded. The reaction time was 1 hour. Reactions with the amount of x(InCl$_3$)<0.58 needed heating with the oil bath, so that IL will catalyse the reaction at a reasonable rate, see Table 7 below. When equal amounts of [C$_4$mim]Cl and InCl$_3$ were used, x(InCl$_3$)=0.50, no reaction occurred at 120° C. When x(InCl$_3$) was 0.52 reaction occurred at 120° C. When x(InCl$_3$) was 0.55 reaction occurred at 80° C. and at 50° C. with x(InCl$_3$) was 0.57. The ionic liquid composition needs to be Lewis acidic otherwise a reaction will not occur.

TABLE 7

The composition of [C$_4$mim]Cl:InCl$_3$ and reaction temperature that was needed for a reaction to occur.

| Reaction | X(InCl$_3$) mol % | Reaction temperature (° C.) |
| --- | --- | --- |
| 1 | 0.5 | 120, no reaction |
| 2 | 0.52 | 120 |
| 3 | 0.55 | 80 |
| 4 | 0.57 | 50 |
| 5 | 0.58 | 20 |
| 6 | 0.60 | 20 |
| 7 | 0.67 | 20 |

Figure 6:
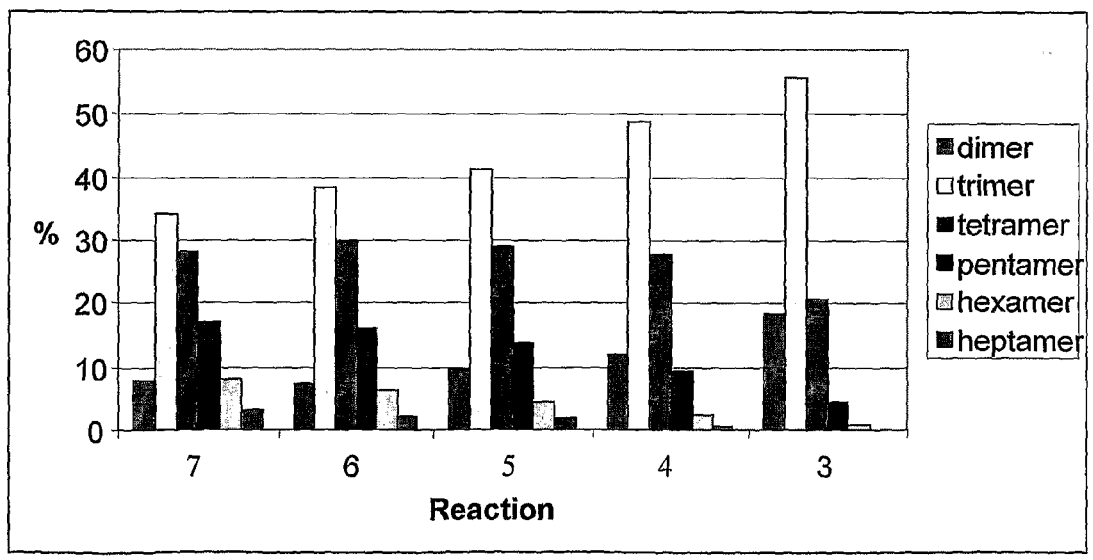
FIG. 6 shows the product distribution of reactions carried out in differing compositions of $[C_4mim]Cl:InCl_3$.

Separation of product layer was done by decantation, as the products didn't dissolve into the ionic liquid phase. Products, from dimers (C$_8$H$_{16}$) to octamers (C$_{32}$H$_{64}$), were formed. When we compare the product distribution of reactions, which were carried out at room temperature, we can see that the greater the amount of InCl$_3$ in the IL, the faster the reaction goes. Results are shown in FIG. 6, see reactions 7, 6 and 5, where amount of x(InCl$_3$)=0.67, 0.6 and 0.58, respectively.

At the same time larger amounts of longer oligomers are formed. The product distribution of reactions in IL's with x(InCl$_3$)=0.57 and 0.55 (Reactions 4 and 3, respectively) are also shown in FIG. 6. No reaction happened in these reactions at room temperature in 3 hours. Heating with an oil bath increases the rate of reaction and also affects the reaction distribution. The higher the temperature the more dimers that are formed. The main products in all reactions are trimer and tetramer.

4.2 Modification of the Reaction Set Up

Some modifications were preferably added to the reaction set up, because previous reactions showed that the dimerisation reaction is very fast. In order to get more dimers, it is preferable to have a weak catalyst and high reaction temperature. And also the contact time between catalyst and isobutene should be as short as possible. The reaction was changed from batchwise addition of isobutene to a continuously fed reaction. This also means that the reactor size could be smaller, because it's not necessary to add all of the gas at the beginning of reaction. Adding the 2-methylpropene continuously also affects the contact time with the catalyst and makes it shorter. The apparatus was modified to use a 25 ml glass tube, which has an inlet on the side and an outlet on the top of the tube. The gas is able to enter the tube, where IL is at the bottom and the reaction mixture is stirred with magnetic stirring bar. Unreacted gas passes to a bubbler through the outlet and a product layer forms-above the IL. The tube, was fitted with a long sidearm that went down to the bottom of the tube, and allowed gaseous starting material to bubble through IL. The modified reaction set ups were tested with [C$_4$mim]Cl:InCl$_3$, x(InCl$_3$)= 0.58.

4.3 Oligomerisations in IL with Composition x(InCl$_3$)=0.58

Figure 7:
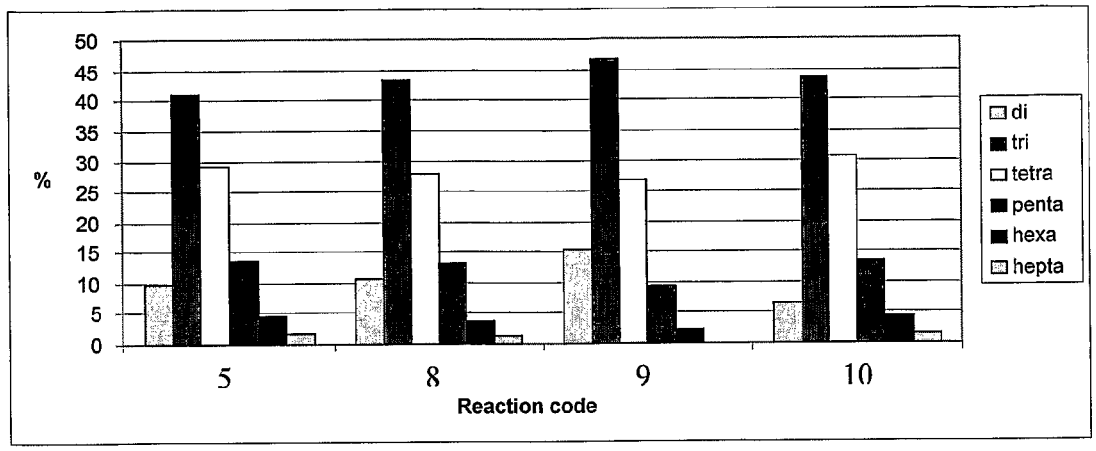
FIG. 7 shows the product distribution of reactions carried out in $[C_4mim]Cl:InCl_3$ wherein $x(InCl_3)=0.58$.

Three reactions were carried out in ionic liquids with composition x(InCl$_3$) 0.58, at room temperature and reaction time was 1 hour. 2-Methylpropene was fed continuously the rate of 1 cm$^3$/min into the reactor. The product distributions of these reactions are shown in FIG. 7. Reaction 8, was done in a 25 ml reactor without a sidearm and the amount of IL was 1 g ([C$_4$mim]Cl 2.5 mmol and InCl$_3$ 3.5 mmol). The conditions of this reaction were the same as for Reaction 5. The product distribution was same in both reactions. The main products were trimers. Reaction 9 was done in the reactor with a sidearm. Reaction conditions were the same as in Reaction 8 (x(InCl$_3$)=0.58, rt, 1 h), but the amount of IL was 2 g ([C$_4$mim]Cl 5 mmol and InCl$_3$ 7.1 mmol). The product distribution changed so that the amount of di- and trimers were increased and the amount of longer oligomers were decreased compared to Reaction 8. The reactor modification of a sidearm increased the amount of dimers. Lastly Reaction 10, was conducted under the same conditions (x(InCl$_3$)=0.58, rt, 1 h) in a reactor with sidearm, with 4 g ([C$_4$mim]Cl 10 mmol and InCl$_3$ 14 mmol). More longer oligomers were formed instead of dimers. These results are shown in FIG. 7.

Figure 8:
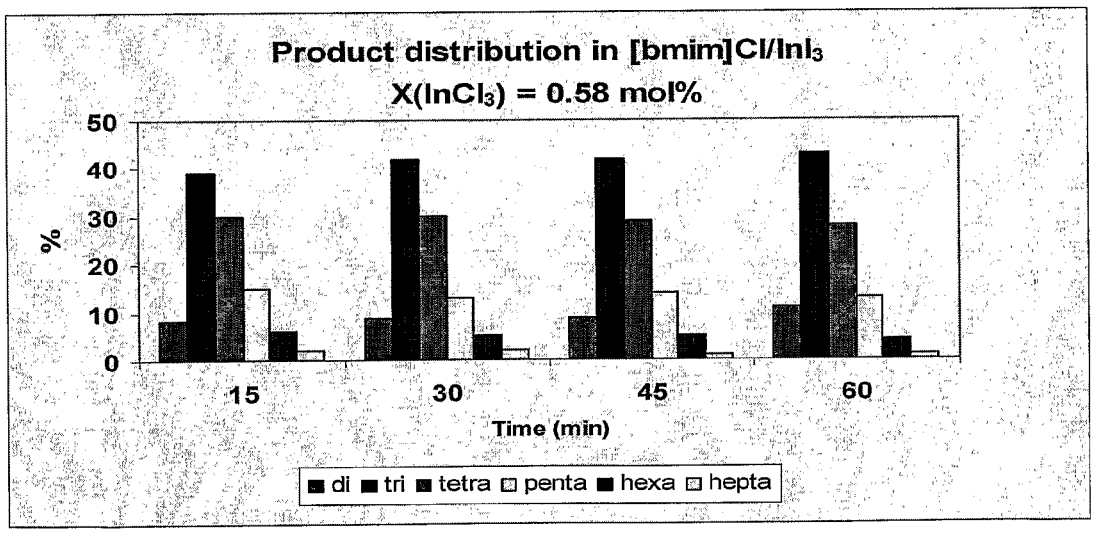
FIG. 8 shows the product distribution of the reaction of $[C_4mim]Cl:InCl_3$ ($x(InCl_3)=0.58$) as a function of time.

The product distribution of Reaction 8 is also shown in FIG. 8. Samples were taken from the reaction every 10 or 15 minutes. Here it can be seen that the product distribution remains similar during the whole reaction.

4.4 Oligomerisations in IL with Composition x(InCl$_3$)=0.55

Reaction in an autoclave showed that when an IL with composition x(InCl$_3$)=0.55 was used, the reaction required heating with an oil bath. A previous reaction in an autoclave, Reaction 11, was carried out at 80° C. The amount of IL was 4 g ([$C_4$mim]Cl 10 mmol and $InCl_3$ 12 mmol) and reaction time was 1 hour. A cold trap was added in to the reaction set up and it was connected with a hose to the reactor. Now the products, which were formed in the reactor, could evaporate out of the reactor to a cold trap. This trap was then placed on an ice bath.

Figure 9:
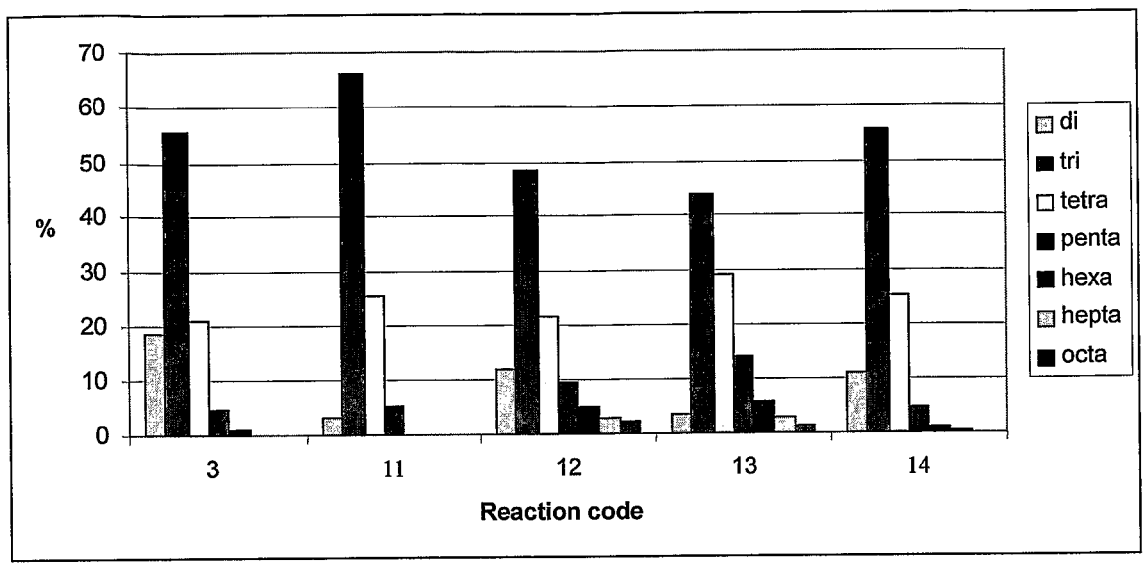
FIG. 9 shows the product distribution of reacting [C$_4$mim]Cl:InCl$_3$ wherein x(InCl$_3$)=0.55.
Figure 10:
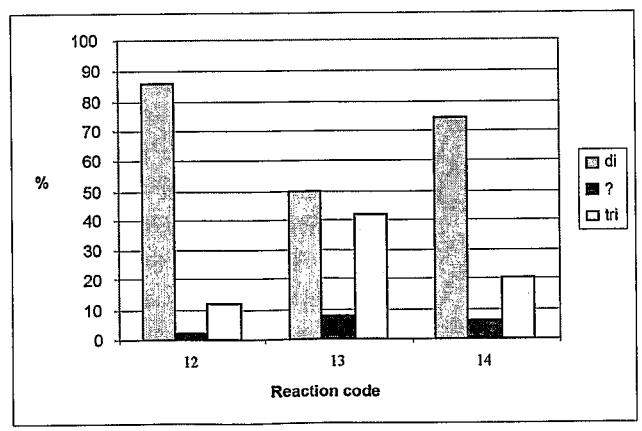
FIG. 10 shows the product distribution wherein the apparatus comprises a cold trap.

In Reactions 12, 13 and 14 the composition was $x(InCl_3)=0.55$ and amount of IL was 4.0 g, and the reaction temperature was higher (120° C.) and the reaction times were 30 min, 30 min and 1 hour, respectively. The product distribution of these reactions is shown in FIG. 9. Samples for GCMS analysis were also taken from the cold trap and product distributions are shown in FIG. 10. It seems that the dimers are easily evaporated from the reactor and also some trimers will be collected in a cold trap. The products were decanted from the reactor and the IL was used again without any purification (Reaction 13). If these two reactions are compared, it can be seen that amount of di- and trimers are reduced and amount of tetra-, penta- and hexamers are greater in Reaction 13. The last Reaction 14, was done with pure ionic liquid and the same reaction conditions, for 1 h. When the product distribution of Reaction 12, with 30 min reaction time was compared with the product distribution of Reaction 14, it can see that amount of dimers is same in both reactions. The amount of tri- and tetramers is greater, and the longer oligomers were less in Reaction 14. Comparing the product distributions of samples from the cold trap we can see that longer reaction time will decrease the amount of dimers and increase the amount of trimers. The analysis with GCMS showed that the amount of isomers of di- and trimers were higher in these reactions with the cold trap and also some products which has molecular mass between di- and trimers were formed, see FIG. 10.

4.5 Dimerization in [$C_2$mim]Cl+$InCl_3$ ($x(InCl_3)=0.60$)

Figure 11:
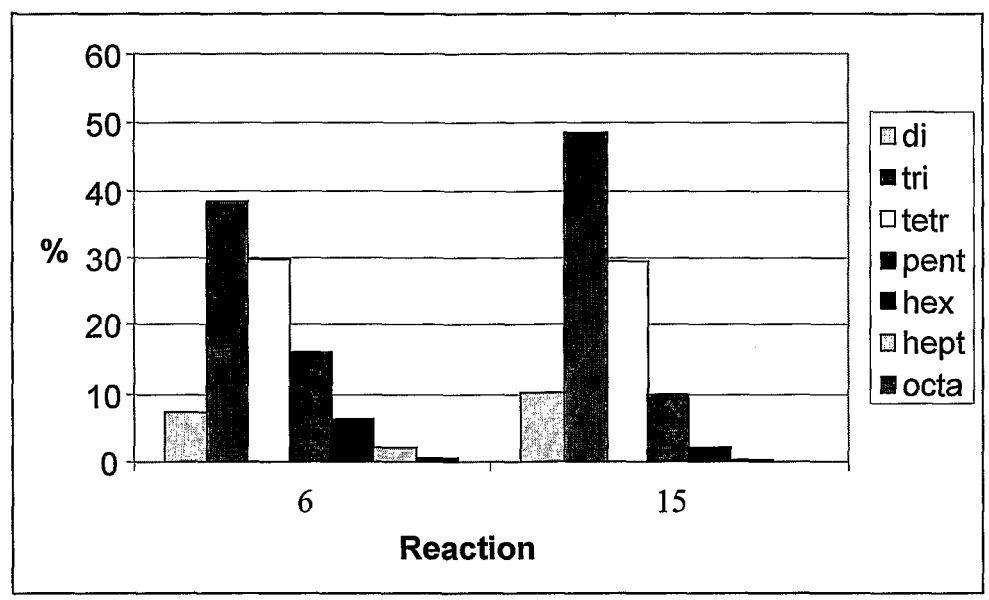
FIG. 11 shows the product distribution of Reaction 15.

One reaction was done in [$C_2$mim]Cl:$InCl_3$ $x(InCl_3)=0.60$, to see the effect of a different ionic liquid for this reaction. This Reaction 15 required heating (50° C.) to proceed, because the ionic liquid has melting point of 43° C. the amount of IL was 1 g and reaction time was 1 hour. The product distribution was different than in [$C_4$mim]Cl:$InCl_3$, $x(InCl_3)=0.60$. The results from this reaction is shown in FIG. 11. Amounts of di- and trimers are higher in this reaction, which was done with [$C_2$mim] cation.

4.6 Supported Ionic Liquids

Two ionic liquids of composition $x(InCl_3)=0.55$ and $x(InCl_3)=0.6$ were prepared by mixing 10 g of [$C_4$mim]Cl with either 15.3 g or 18.9 g $InCl_3$ respectively, to form a white ionic liquid (compound or mixture).

The ($x(InCl_3)=0.55$) indium chloride ionic liquid (2.0 g) was dissolved in methanol (100 ml) and flash silica (10 g was added). This was thoroughly mixed and the methanol was removed on a rotary evaporator at 100 mBar, 50° C. The supported ionic was activated by heating at 100° C. at 0.1 mBar for 4 hours. This was labelled as 20% $x(InCl_3)=0.55$ [$C_4$mim]Cl/$InCl_3$.

The ($x(InCl_3)=0.60$) indium chloride ionic liquid (4.0 g) was dissolved in methanol (100 ml) and flash silica (10 g was added). This was thoroughly mixed and the methanol was removed on a rotary evaporator at 100 mBar, 50° C. The supported ionic was activated by heating at 100° C. at 0.1 mBar for 4 hours. This was labelled as 40% $x(InCl_3)=0.60$ [$C_4$mim]Cl/$InCl_3$.

4.6.1 Reactions on Supported Ionic Liquids

Figure 15:
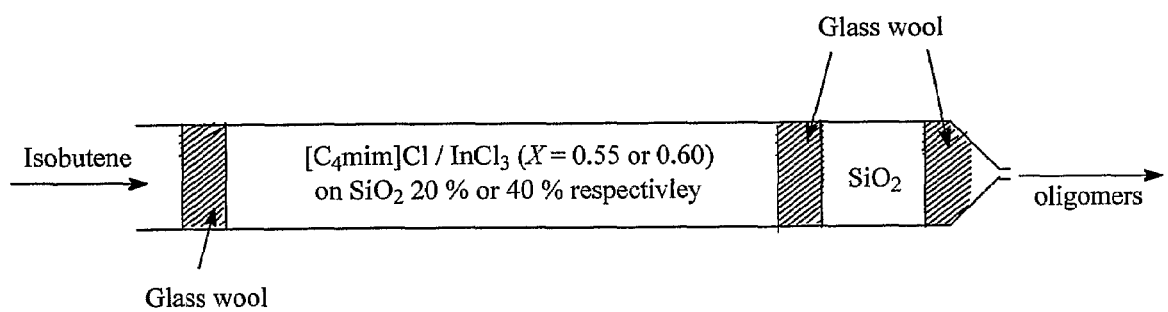
FIG. 15 is a diagrammatic view of a reaction tube for use in oligomerisation reactions.

The ionic liquids were loaded into a tube with a narrow and hollow end as in FIG. 15. The dimensions are: glass tube internal diameter=8 mm, length of packed supported ionic liquid=200 mm, length of packed $SiO_2$=20 mm, lengths of glass wool=10 mm.

Figure 16:
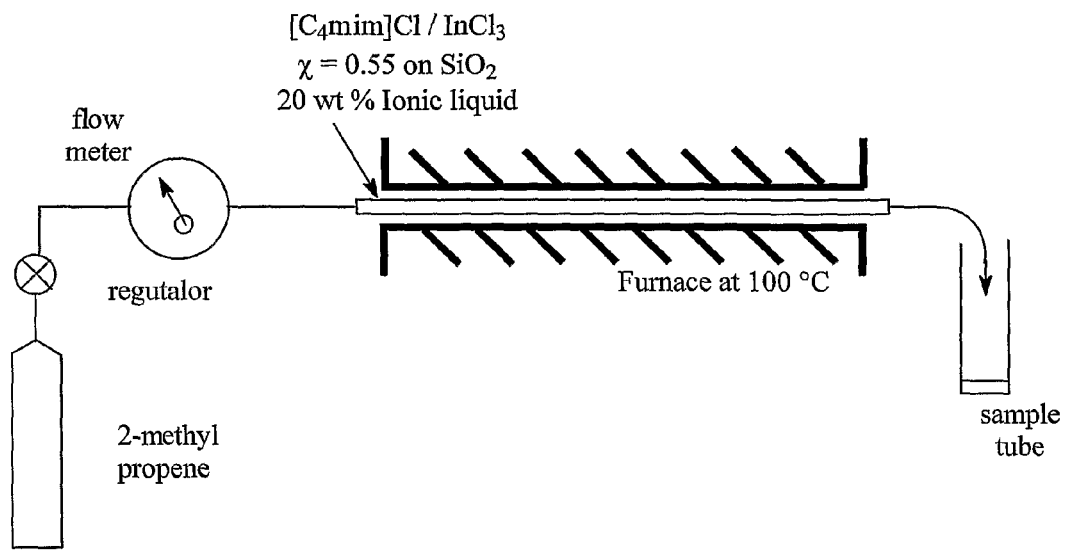
FIG. 16 is a diagrammatic view of an apparatus for use in oligomerisation.

4.6.2 Reaction of Isobutene with 20% ($x(InCl_3)=0.55$) [$C_4$mim]Cl/$InCl_3$ The tube was prepared as in 4.6.1 and isobutene was passed through the tube reactor in a tube oven at 10° C., at 1, 3, and 10 $cm^3$ per second (see FIG. 16). After 10 minutes, the oligomerised product was analysed by gas chromatography (column=Restec RTX-5) and proton NMR spectroscopy (see below for the chromatogram and spectra at the three different flow rates).

Figure 17:
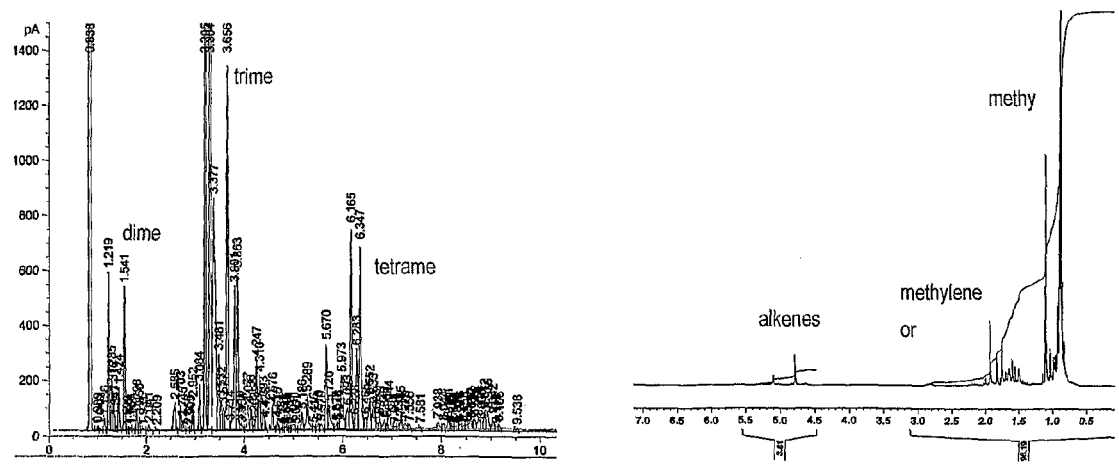
FIG. 17 is an NMR spectrum of products produced during oligomerisation at a temperature of 180° C. and a flow rate of 1 cm$^3$.
Figures 18, 19:
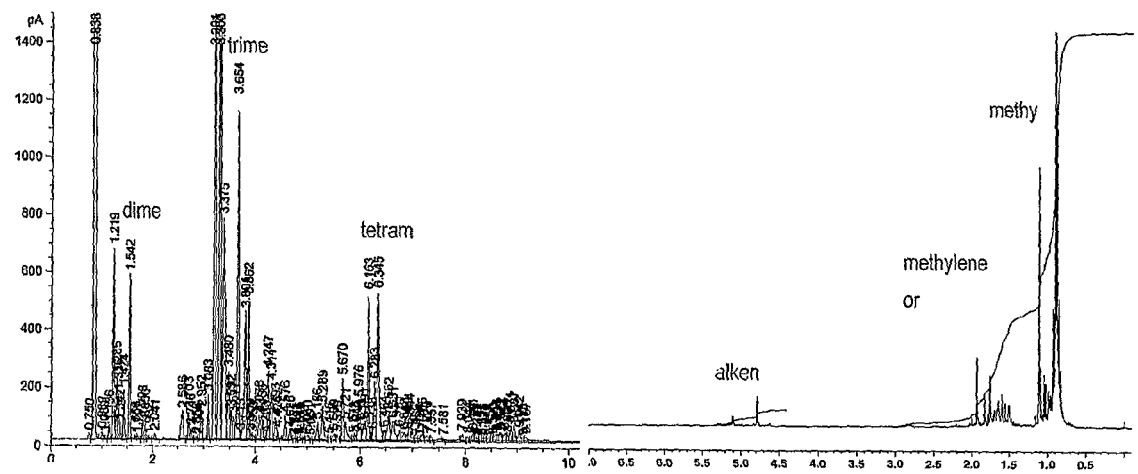
FIG. 18 is an NMR spectrum of products produced during oligomerisation at a temperature of 180° C. and a flow rate of 3 cm$^3$.
FIG. 19 is an NMR spectrum of products produced during oligomerisation at a temperature of 180° C. and a flow rate of 10 cm$^3$.
Figure 20:
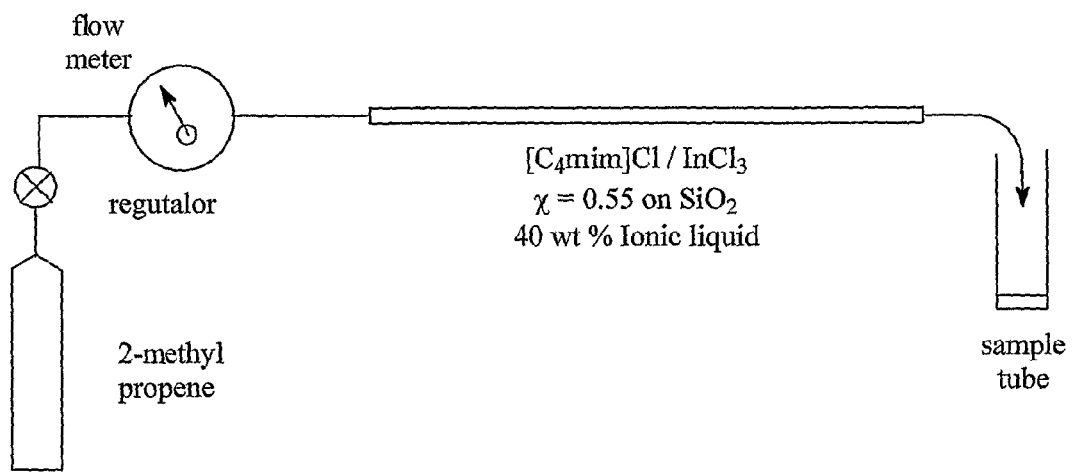
FIG. 20 is a diagrammatic view of an apparatus for use in room temperature oligomerisation.

As can be seen in FIGS. 17 to 19 as the flow rate increases, the proportion of low molecular weight oligomers is increased.

4.6.3 Reaction of Isobutene with 40% ($x(InCl_3)=0.60$) [$C_4$mim]Cl/$InCl_3$ The tube was prepared as in 4.6.1 and isobutene was passed through the tube reactor in a tube oven at room temperature at 1 $cm^3$ and 10 $cm^3$ per second (see Diagram 20). After 10 minutes, the oligomerised product was analysed by gas chromatography (column=Restec RTX-5). See below for the chromatogram and spectra at the three different flow rates.

Figure 21:
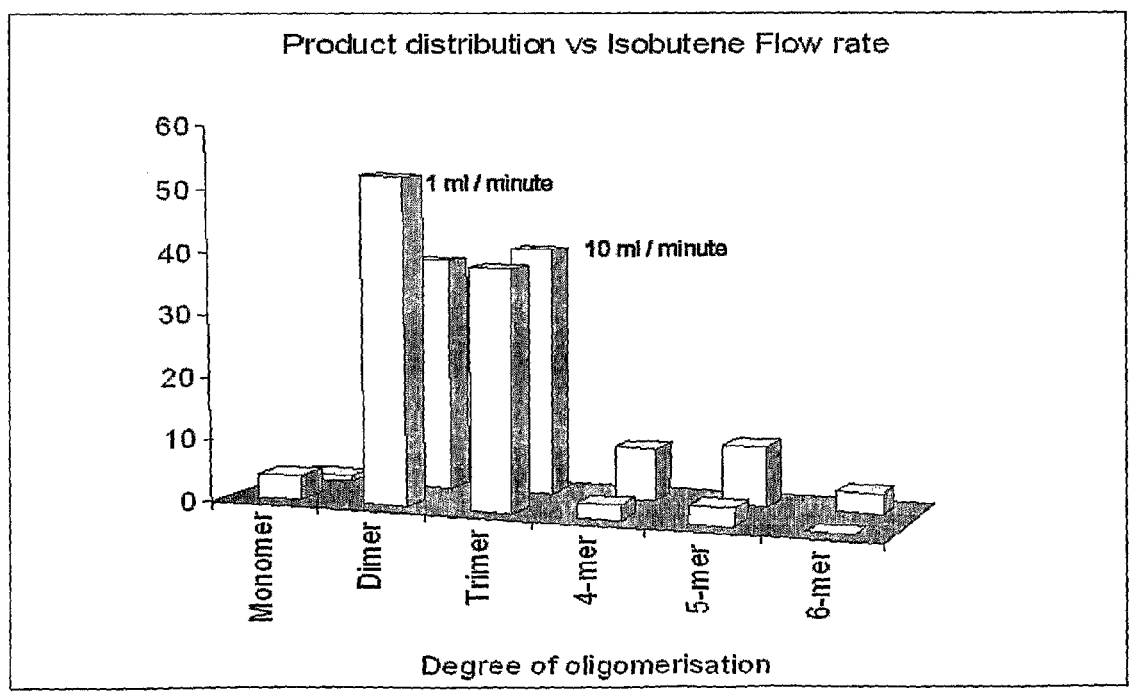
FIG. 21 shows a comparison between product distribution and isobutene flow rate for room temperature oligomerisation.

As can be seen from FIG. 21, the dimer is the major product of the reaction at 10 ml per minute and the proportion of the 4-, 5-, and 6-mers is 5%. The degree of oligomerisation rises if the flow rate is reduced to 1 ml per minute. Here the proportion of the 4-, 5-, and 6-mers is 20%.

4.6 Conclusions

The oligomerisation reactions show that modification of the reaction setup, composition of catalytic ionic liquid, reaction temperature and also the type of cations of ionic liquid will affect the product distribution:

- The modification of reaction setup to include a cold trap makes separation of the products easier.
- The temperature of cold trap should be such that it will collect dimers (and trimers), but it will let gas go through. Such temperatures are of course selectable by the person skilled in the art.
- The gas flow rate can be adjusted such that it will be fast enough to carry formed dimers into the cold trap.
- Unreacted isobutene can be recycled back to the reactor.
- It is possible to put 2 or more cold traps in line, wherein another would collect dimers and/or trimers.
- The reaction works well if the catalyst is supported on a solid support.
- Suitable supports are silica, or any other solid which does not interfere with the ionic liquid or deactivate it.
- Flow rates, ionic liquid composition, time, dimensions of the reactor, length and quantity of supported ionic liquid, pressure and temperature, all affect the degree of oligomerisation and isomerisation.

The invention claimed is:
1. A process for the selective oligomerisation of $C_2$ to $C_{20}$ linear or branched alkenes, wherein the reaction takes place in the presence of a indium(III) chloride ionic liquid of formula:

[Cat$^+$][X]:InCl$_3$ wherein:
Cat$^+$ is: a cationic species selected from imidazolium, pyridinium, pyrazolium, thiazolium, isothiazolinium, oxothiazolium, oxazinium, oxasolium, dithiazolium, triazolium, selenozolium, oxaphospholium, furanium, thiophenium, phospholium, pentazolium, indolium, indolinium, iso-oxazolium, iso-triazolium, tetrazolium, benzofuranium, thiadiazolium, pyrimidinium, pyrazinium, pyridazinium, piperazinium, piperidinium, morpholinium, pyranium, phthalazinium, quinazolinium, quinolinium, isoquinolinium, oxazinium, and pyrrolidinium, diazabicycloundecenium, diazabicyclononenium, diazabicyclodecenium, or triazadecenium;

[N(R$^a$)(R$^b$)(R$^c$)(R$^d$)]$^+$; or [P(R$^a$)(R$^b$)(R$^c$)(R$^d$)]$^+$ wherein R$^a$, R$^b$, R$^c$, and R$^d$ can be the same or different, and are each independently selected from $C_1$ to $C_{40}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_1$ to $C_6$ alkoxy, $C_6$ to $C_{10}$ aryl, CN, OH, NO$_2$, $C_7$ to $C_{30}$ aralkyl and $C_7$ to $C_{30}$ alkaryl;
X is an anionic species;
wherein the mole fraction of InCl$_3$ in the ionic liquid is greater than or equal to 0.50;
wherein the ionic liquid is supported on a solid support
and wherein the reaction is selective for the formation of dimers, trimers, and/or tetramers.

2. A process according to claim 1, wherein Cat$^+$ is neutral, acidic or basic.

3. A process according to claim 1, wherein Cat$^+$ is selected from:—

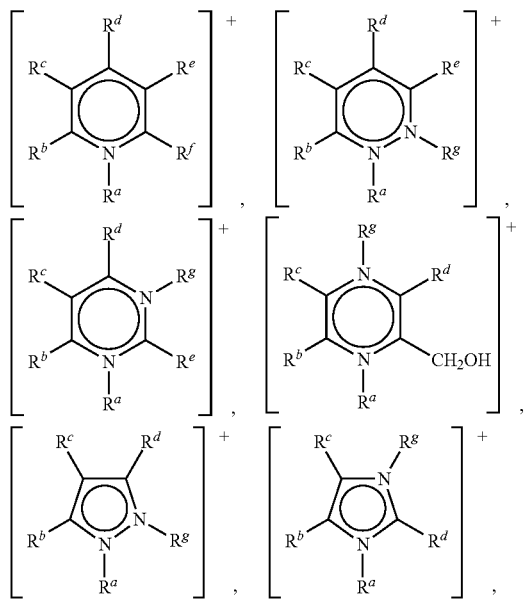

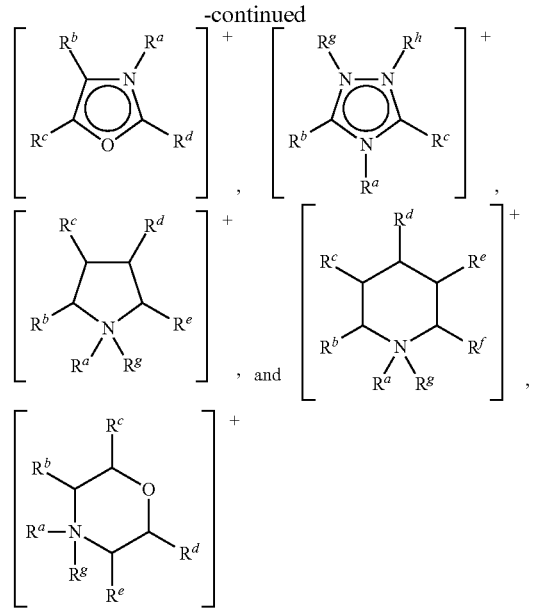

wherein:
R$^a$, R$^b$, R$^c$, R$^d$, R$^e$, R$^f$, R$^g$ and R$^h$ can be the same or different, and are each independently selected from hydrogen, a $C_1$ to $C_{40}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_6$ to $C_{10}$ aryl, CN, OH, NO$_2$, $C_7$ to $C_{30}$ aralkyl and $C_7$ to $C_{30}$ alkaryl, or any two of R$^b$, R$^c$, R$^d$, R$^e$ and R$^f$ attached to adjacent carbon atoms form a methylene chain —(CH$_2$)$_q$— wherein q is from 8 to 20.

4. A process according to claim 3, wherein Cat$^+$ is selected from:

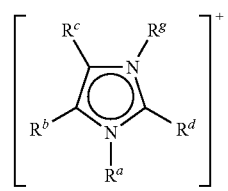

wherein:
R$^a$, R$^b$, R$^c$, R$^d$, and R$^g$ are as defined in claim 3.

5. A process according to claim 4, wherein R$^b$, R$^c$ and R$^d$ are each hydrogen; and R$^a$ and R$^g$ are selected from $C_1$ to $C_{20}$, linear or branched, alkyl, and one of R$^a$ and R$^g$ may be hydrogen.

6. A process according to claim 5, wherein one of R$^a$ and R$^g$ is hydrogen or methyl; and the other is selected from $C_1$ to $C_{20}$ linear or branched alkyl.

7. A process according to claim 6, wherein one of R$^a$ and R$^g$ is hydrogen or methyl, and the other is selected from $C_1$ to $C_{18}$ linear or branched alkyl.

8. A process according to claim 7, wherein one of R$^a$ and R$^g$ is hydrogen or methyl, and the other is selected from methyl, ethyl, butyl, hexyl, octyl, decyl, dodecyl, tetradecyl, hexadecyl and octadecyl.

9. A process to claim 3, wherein Cat$^+$ is selected from: methylimidazolium, 1,3-dimethylimidazolium, 1-ethyl-3- dimethylimidazolium, 1-butyl-3-dimethylimidazolium, 1-hexyl-3-methylimidazolium, 1-octyl-3-methylimidazolium, 1-decyl-3-methylimidazolium, 1-dodecyl-3-methylimidazolium, 1-methyl-3-tetradecylimidazolium, 1-hexadecyl-3-methylimidazolium and 1-methyl-3-octadecylimidazolium.

10. A process according to claim 3, wherein Cat$^+$ is selected from: 1-butylpyridinium, 1-hexylpyridinium, 1-octylpyridinium, 1-decylpyridinium, 1-dodecylpryridinium, 1-tetradecylpyridinium, 1-hexadecylpyridinium and 1-octadecylpyridinium.

11. A process according to claim 3, wherein Cat$^+$ is selected from 1-methyl-1-butylpyrrolidinium, 1-methyl-1-hexylpyrrolidinium, 1-methyl-1-octylpyrrolidinium, 1-methyl-1-decylpyrrolidinium, 1-methyl-1-dodecylpyrrolidinium, 1-methyl-1-tetradecylpyrrolidinium, 1-methyl-1-hexadecylpyrrolidinium and 1-methyl-1-octadecylpyrrolidinium.

12. A process according to claim 1, wherein Cat$^+$ is selected from:

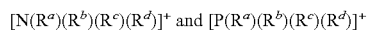

wherein:
R$^a$, R$^b$, R$^c$, and R$^d$ can be the same or different, and each are independently selected from, C$_1$ to C$_{20}$, straight chain or branched alkyl group, a C$_3$ to C$_6$ cycloalkyl group, or a C$_6$ to C$_8$ aryl group, wherein said alkyl, cycloalkyl or aryl groups are unsubstituted or may be substituted by one to three groups selected from: C$_1$ to C$_6$ alkoxy, C$_1$ to C$_6$ alkoxy, C$_6$ to C$_{10}$ aryl, CN, OH, NO$_2$, C$^7$ to C$_{30}$ aralkyl and C$_7$ to C$_{30}$ alkaryl.

13. A process according to claim 12, wherein Cat$^+$ is selected from: tetrasubstituted ammonium, tetramethyl ammonium, tetraethyl ammonium, tetrapropyl ammonium, tetrabutyl ammonium, tetrapentyl ammonium, tetrahexyl ammonium, 2-hydroxyethyl-trimethyl ammonium and ethers thereof, tetrasubstituted phosphinium, tetraethyl phosphinium, tetrapropyl phosphinium, tetrabutyl phosphiniium, tetrapentyl phosphinium, tetrahexyl phosphinium.

14. A process according to claim 1, wherein X$^-$ is selected from: F$^-$, Cl$^-$, Br$^-$ or I$^-$, HSO$_4^-$, H$_2$PO$_4^-$, HPO$_4^{2-}$, OSO$_2$CH$_3^-$, OSO$_2$(C$_6$H$_4$)CH$_3^-$, OSO$_3$CH$_3^-$, OSO$_3$C$_2$H$_5^-$, SO$_4^{2-}$.

15. A process according to claim 14, wherein X$^-$ is Cl$^-$.

16. A process according to claim 1, wherein the unsaturated hydrocarbon is a C$_2$ to C$_{10}$ linear or branched alkene.

17. A process according to claim 16, wherein the unsaturated hydrocarbon is a C$_2$ to C$_5$ linear or branched alkene.

18. A process according to claim 17, wherein the unsaturated hydrocarbon is isobutene.

19. A process according to claim 1, wherein the reaction is selective for the formation of dimers.

20. A process according to claim 19, wherein the mole fraction of InCl$_3$ in the ionic liquid is from 0.50 to 0.55.

21. A process according to claim 19, wherein the reaction temperature is at least 120° C.

22. A process according to claim 19, further comprising the step of separating the dimers from the reaction mixture.

23. A process according to claim 22, wherein the dimers are evaporated from the reaction mixture and collected by a cold trap.

24. A process according to claim 1, wherein the reaction is selective for the formation of trimers and/or tetramers.

25. A process according to claim 24, wherein the mole fraction of InCl$_3$ in the ionic liquid is from 0.50 to 0.67.

26. A process according to claim 24, wherein the reaction temperature is at least 20° C.

27. A process according to claim 26, wherein the reaction temperature is from 20° C. to 120° C.

28. A process according to claim 27, wherein the reaction temperature is from 50° C. to 120° C.

29. A process according to claim 26, wherein the reaction temperature is greater than 120° C.

30. A process according to claim 24, wherein the process includes a separation step using a cold trap.

31. A process according to claim 1, wherein the solid support is selected from particulated metal oxides, zeolites, mixed metal oxides, oxides of silicon, aluminium, titanium or germanium, polymers, and mixtures thereof.

32. A process according to claim 31, wherein the solid support is selected from alumina, silica, aluminosilicates, clay, and particulated polyolefins.

33. A process according to claim 32, wherein the solid support is silica.

34. A process according to claim 1 wherein the supported ionic liquid is produced by a process comprising the steps of:
dissolving the ionic liquid in a solvent;
adding a solid support; and
removing the solvent.

35. A process according to claim 34, wherein the solvent is methanol.

36. A process according to claim 34, wherein the solid support is silica.

37. A process according to claim 34, wherein the solvent is removed by evaporation.

38. A process according to claim 34, wherein the supported ionic liquid is heated under reduced pressure.

39. A process according to claim 38, wherein the supported ionic liquid is heated to 100° C. for 1 hour at a pressure of 133.3 Pa (1 mmHg).

* * * * *